United States Patent
Zhang

(10) Patent No.: US 9,738,605 B2
(45) Date of Patent: Aug. 22, 2017

(54) HYBRID COMPOUNDS OF CURCUMIN AND MELATONIN AS NEUROPROTECTANTS FOR NEURODEGENERATIVE DISORDERS

(71) Applicant: VIRGINIA COMMONWEALTH UNIVERSITY, Richmond, VA (US)

(72) Inventor: Shijun Zhang, Richmond, VA (US)

(73) Assignee: Virginia Commonwealth University, Richmond, VA (US)

( * ) Notice: Subject to any disclaimer, the term of this patent is extended or adjusted under 35 U.S.C. 154(b) by 0 days.

(21) Appl. No.: 15/034,223

(22) PCT Filed: Nov. 7, 2014

(86) PCT No.: PCT/US2014/064462
§ 371 (c)(1),
(2) Date: May 4, 2016

(87) PCT Pub. No.: WO2015/069970
PCT Pub. Date: May 14, 2015

(65) Prior Publication Data
US 2016/0289187 A1 Oct. 6, 2016

Related U.S. Application Data

(60) Provisional application No. 61/901,204, filed on Nov. 7, 2013.

(51) Int. Cl.
*C07D 209/16* (2006.01)
(52) U.S. Cl.
CPC ................ *C07D 209/16* (2013.01)

(58) Field of Classification Search
CPC .................................................. C07D 209/16
See application file for complete search history.

(56) References Cited

U.S. PATENT DOCUMENTS

| 7,906,643 B2 | 3/2011 | DiMauro | |
|---|---|---|---|
| 2013/0156705 A1* | 6/2013 | Zhang | A61K 31/4192 424/9.6 |

OTHER PUBLICATIONS

Spuch et al., "A new tacrine-melatonin hybrid reduces amyloid burden and behavioral deficits in a mouse model of Alzheimer's disease", Neurotoxicity Research, 2010, pp. 421-431, vol. 17, No. 4.

Ray et al., "Neuroinflammation in Alzheimer's disease: different molecular targets and potential therapeutic agents including curcumin", Current Opinion in Pharmacology, 2009, pp. 434-444, vol. 9, No. 4.

Chojnacki et al., "Discovery of 5-(4-hydroxyphenyl)-3-oxo-pentanoic acid [2-(5-methoxy-1H-indol-3-yl)-ethyl]-amide as a neuroprotectant for Alzheimer's disease by hybridization of curcumin and melatonin", ACS Chemical Neuroscience, May 2014, pp. 690-699, vol. 5.

\* cited by examiner

*Primary Examiner* — Erich A Leeser
(74) *Attorney, Agent, or Firm* — Whitham, Curtis & Cook, P.C.

(57) ABSTRACT

Hybrid compounds of curcumin and melatonin as neuroprotectants are provided. The hybrid compounds are useful for the treatment and/or prevention of Alzheimer's disease (AD), as well as other neurodegenerative diseases. The hybrid compounds exhibited superior and potent neuroprotection in an AD model.

30 Claims, 20 Drawing Sheets

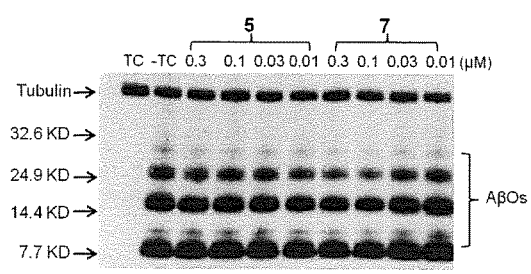
Figure 5A
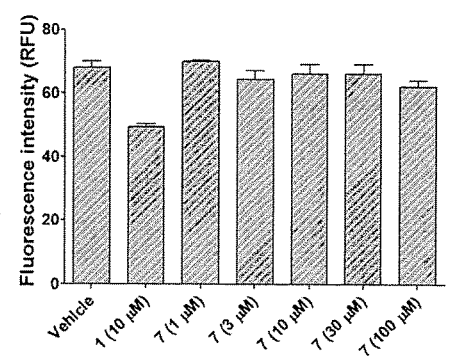
Figure 5B
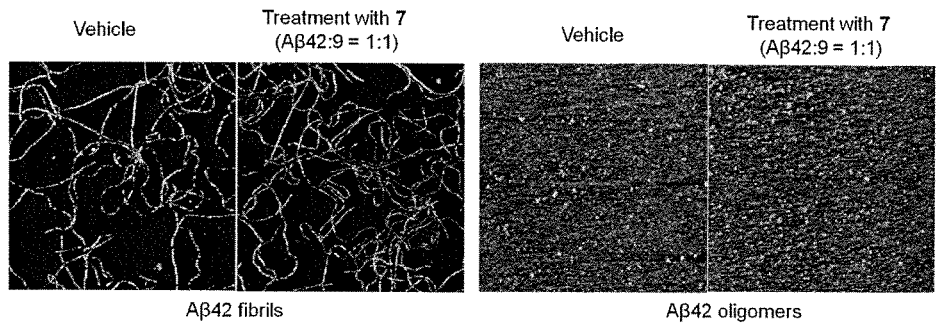
Aβ42 fibrils
Figure 5C
Aβ42 oligomers
Figure 5D

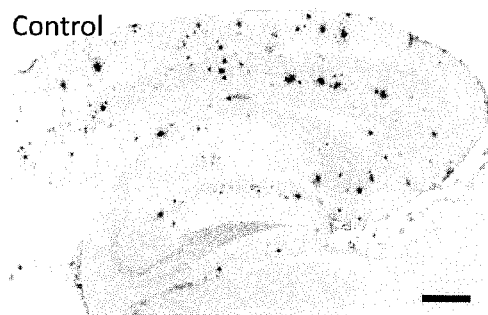
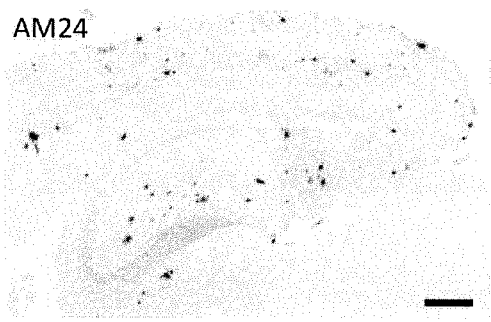
Figure 8A
Figure 8B
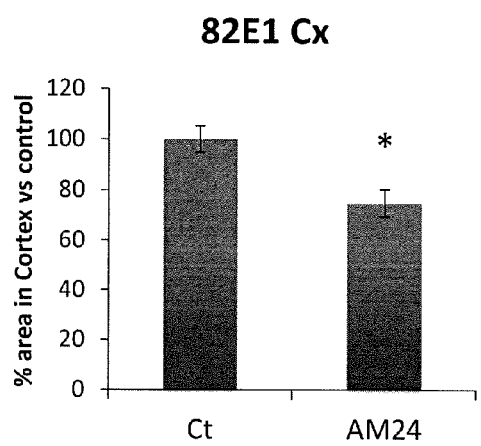
Figure 8C
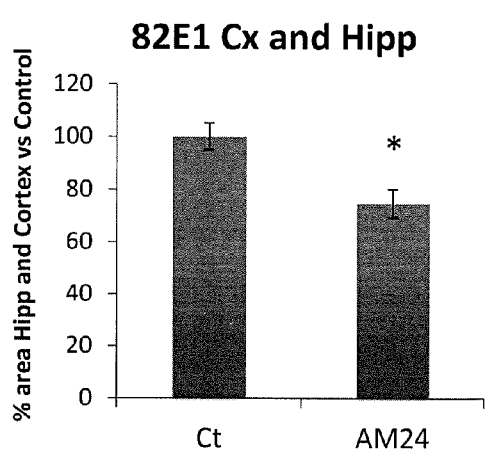
Figure 8D Control

AM24

GFAP

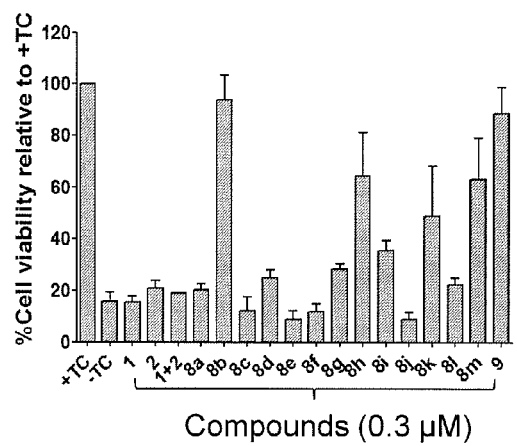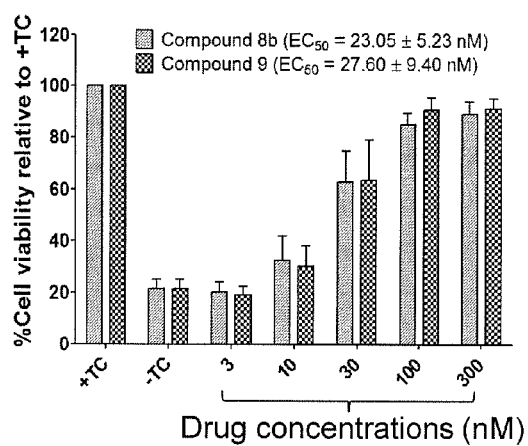
Figure 19A
Figure 19B

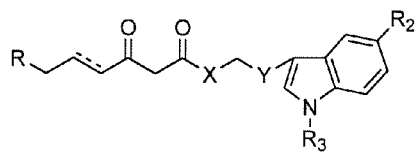
Figure 20A
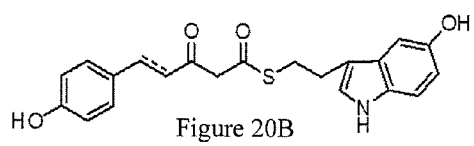
Figure 20B
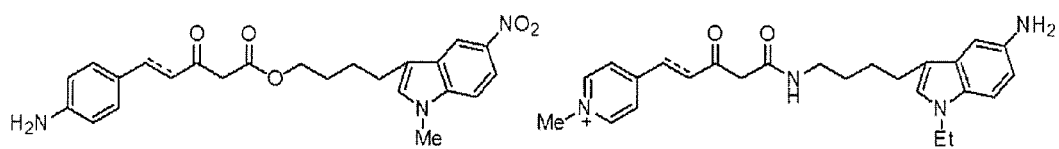
Figure 20C
Figure 20D
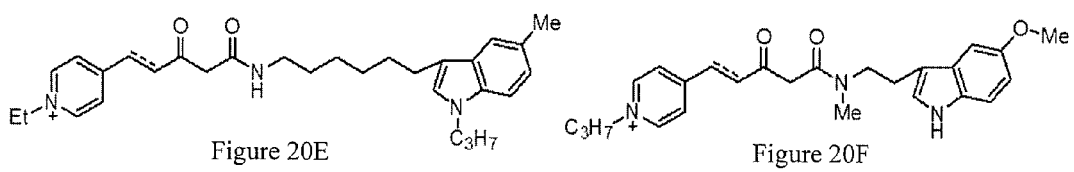
Figure 20E
Figure 20F
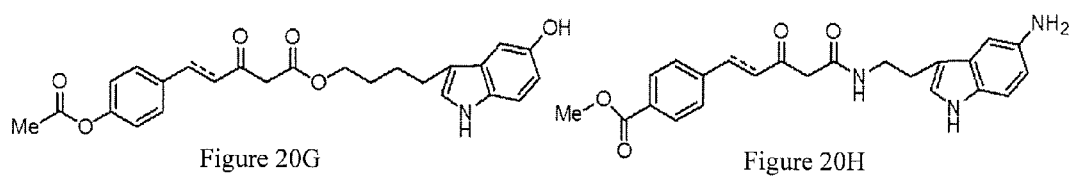
Figure 20G
Figure 20H
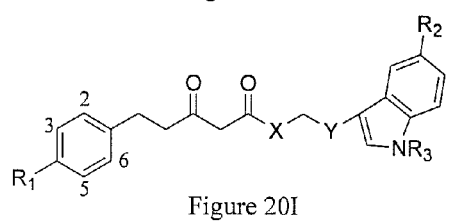
Figure 20I
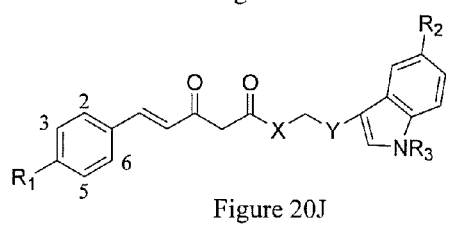
Figure 20J

HYBRID COMPOUNDS OF CURCUMIN AND MELATONIN AS NEUROPROTECTANTS FOR NEURODEGENERATIVE DISORDERS

BACKGROUND OF THE INVENTION

Field of the Invention

Embodiments of the invention generally relate to compounds that are useful for the treatment and/or prevention of neurodegenerative disorders such as Alzheimer's disease. In particular, the invention provides novel hybrid compounds of curcumin and melatonin, and uses thereof.

Background of the Invention

Alzheimer's disease (AD) is a progressive neurodegenerative disorder and the most common cause of dementia. It is estimated that 5.2 million Americans of all ages and up to 30 million individuals worldwide are affected by AD[1]. In addition to the human cost, more than $200 billion is spent annually on AD treatment, significantly exacerbating problems with the overextended U.S. health care economy. Current AD treatments provide mainly symptomatic relief and there are no agents available to delay or cure this disease. The etiology of AD still remains elusive and multiple factors including beta-amyloid (Aβ) aggregates[2], soluble Aβ oligomers (AβOs)[3-5], dyshomeostasis of biometals, oxidative stress, and neuroinflammation[6,7], have been implicated in the development of AD. Recently, the multifunctional strategy of small molecule design has attracted extensive attention in overcoming the limitations of the traditional "one molecule, one target" approach in the development of effective AD treatments, given its multifactorial nature[8,9]. However, rational design of small molecules with therapeutic polypharmacology has always been a challenging task. Therefore, an efficient strategy that helps to identify novel chemical templates would be of great value in surmounting the paucity of effective disease-modifying agents in the pipeline of AD therapeutics.

Natural products have proven to be reliable resources in providing effective therapeutics for a variety of diseases. Curcumin and melatonin have been implicated as potential AD treatment agents by extensive studies[10-13]. Curcumin (1, FIG. 1), a yellow spice and pigment isolated from the rhizome of *Curcuma longa*, has been traditionally and widely used as a food coloring additive. Recently, curcumin has attracted extensive attention in biomedical research as multiple biological activities of curcumin have been revealed including antioxidant, anti-inflammatory, biometal chelating, anti-proliferative, and anti-Aβ activities, among others. As oxidative stress, neuroinflammation, dyshomeostasis of metals, and Aβ have been implicated in the pathology of AD, 1 has been tested in various AD models. Both in vitro and in vivo studies have shown that 1 prevented Aβ-induced toxicity, lowered the level of Aβ in the brain as well as the level of inflammatory cytokines and oxidative stress, thus demonstrating the potential of 1 as a promising candidate for treating human AD[14]. However, due to its poor solubility, bioavailability, and gastrointestinal side effects, further development of 1 as an effective agent for AD is limited. Therefore new analogs of 1 with improved efficacy and pharmacokinetic properties would be of great value for AD patients.

Melatonin (2, FIG. 1), the major secretory product of the pineal gland, plays an essential role in the regulation of circadian rhythms[15]. In addition, 2 can be produced in various tissues and organs, and participates in diverse functions through both receptor-dependent and independent ways, including free radical scavenging, immune response, and mood monitoring, among others[13, 16]. Notably, circadian dysfunction and the reduction of 2 have been observed in AD, thus suggesting the potential of 2 in AD treatment[17,18]. Indeed, 2 has been tested as a potential treatment for AD[19]. In transgenic AD mouse models, 2 has also been shown to improve cognition and reduce Aβ deposition and neuroinflammation[19,20]. Clinical studies of 2 in AD patients also suggested beneficial effects, especially in sleep quality, reduced sundowning, etc.[21] However, more studies are needed to explore and investigate the usefulness of 2 as a treatment for AD. Furthermore, 2 has a relatively short half-life (<30 min), thus novel analogs that retain the multifunctional properties of 2, with improved pharmacokinetic properties, are needed for further investigation and development.

SUMMARY OF THE INVENTION

Herein, hybrids of curcumin and melatonin are presented as innovative and effective neuroprotective compounds and AD-modifying agents. Embodiments of the invention relate to a hybrid strategy that provides novel chemical scaffolds that retain the multifunctional nature of curcumin and melatonin, or possibly with new mechanisms of action, while providing certain advantages, such as 1) enhanced potency by self-synergy within one molecule that is not achievable by a traditional combination of separately dosed agents; and 2) improved pharmacokinetic properties and reduced toxic side effects compared to the administration of multiple agents. Additionally, such hybrid molecules provide the advantages of reduced cost and improved patient compliance, which are sometimes as significant as drug resistance and toxicity. Thus, these compounds, depicted in generic Formula I and Formula II (FIGS. 20I and J), are potent neuroprotectants and represent novel therapeutic agents, such as disease-modifying agents for AD.

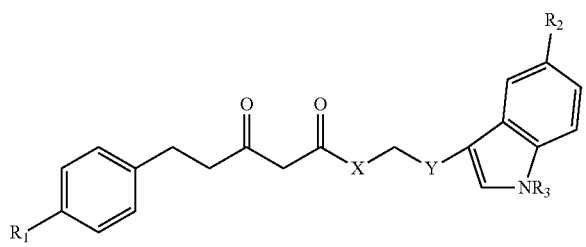

Formula I

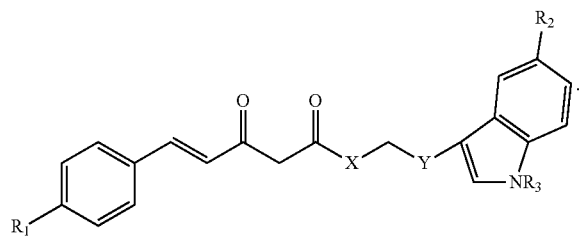

Formula II

It is an object of this invention to provide a compound of Formula I:

Formula I

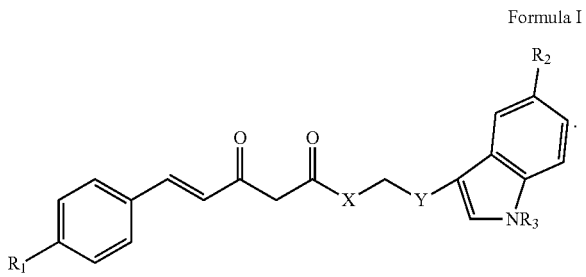

In Formula I,

R1 is selected from the group consisting of: H, OH and NH$_2$ and substituted-N wherein the substituent is selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano;

R2 is selected from the group consisting of H, OH, NH$_2$, NO$_2$ and C$_1$-C$_8$ alkoxyl;

R3 is selected from the group consisting of H and C$_1$-C$_4$ alkyl;

X is S or O or NH or substituted-N, wherein the substituent is selected from the group consisting of C$_1$-C$_8$ alkyl, isopropyl, tert-butyl, saturated or unsaturated monocyclic ring with ring size ranging from 3-7, and unsubstituted or substituted phenyl ring which is optionally substituted with one or more substituents selected from the group consisting of C$_1$-C$_8$ alkyl, C$_1$-C$_8$ alkoxyl, C$_1$-C$_8$ alkylcarbonyl, halogen, hydroxyl, amino, nitro, and cyano; and Y is selected from the group consisting of C$_1$-C$_4$ alkyl.

It is also an object of this invention to provide a compound of Formula II:

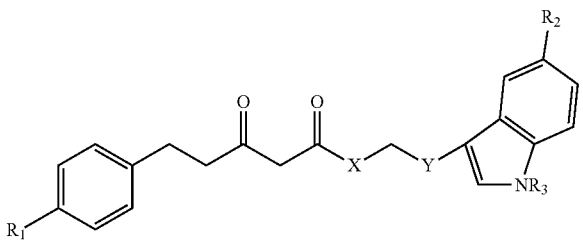

In Formula II,

R1 is selected from the group consisting of: H, OH and NH$_2$ and substituted-N wherein the substituent is selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano;

R2 is selected from the group consisting of H, OH, NH$_2$, NO$_2$ and C$_1$-C$_4$ alkoxyl;

R3 is selected from the group consisting of H and C$_1$-C$_4$ alkyl;

X is S or O or NH or substituted-N, wherein the substituent is selected from the group consisting of: C$_1$-C$_8$ alkyl, isopropyl, tert-butyl, saturated or unsaturated monocyclic ring with ring size ranging from 3-7, and unsubstituted or substituted phenyl ring which is optionally substituted with one or more substituents selected from the group consisting of: C$_1$-C$_8$ alkyl, C$_1$-C$_8$ alkoxyl, C$_1$-C$_8$ alkylcarbonyl, halogen, hydroxyl, amino, nitro, and cyano; and Y is selected from the group consisting of C$_1$-C$_4$ alkyl.

Embodiments of the invention also provide a method of preventing or treating neurodegenerative disorders, in particular Alzheimer's disease (AD), in a patient in need thereof. The method comprises the step of administering to the patient a therapeutic amount of at least one of a compound of Formula I or Formula II:

Formula I

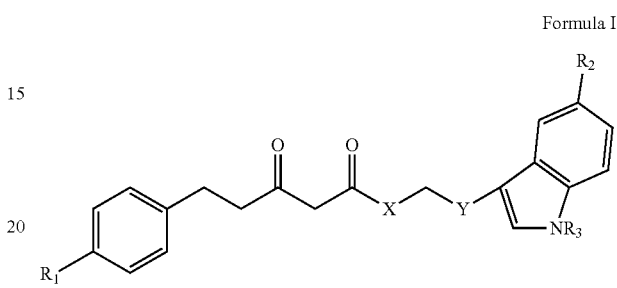

Formula II

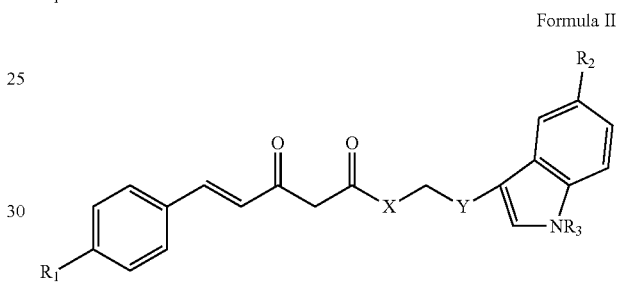

In Formula I,

R1 is selected from the group consisting of: H, OH and NH$_2$ and substituted-N wherein the substituent is selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano;

R2 is selected from the group consisting of H, OH, NH$_2$, NO$_2$ and C$_1$-C$_8$ alkoxyl;

R3 is selected from the group consisting of H and C$_1$-C$_4$ alkyl;

X is S or O or NH or substituted-N, wherein the substituent is selected from the group consisting of C$_1$-C$_8$ alkyl, isopropyl, tert-butyl, saturated or unsaturated monocyclic ring with ring size ranging from 3-7, and unsubstituted or substituted phenyl ring which is optionally substituted with one or more substituents selected from the group consisting of C$_1$-C$_8$ alkyl, C$_1$-C$_8$ alkoxyl, C$_1$-C$_8$ alkylcarbonyl, halogen, hydroxyl, amino, nitro, and cyano; and Y is selected from the group consisting of C$_1$-C$_4$ alkyl.

In Formula II,

R1 is selected from the group consisting of: H, OH and NH$_2$ and substituted-N wherein the substituent is selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano;

R2 is selected from the group consisting of H, OH, NH$_2$, NO$_2$ and C$_1$-C$_8$ alkoxyl;

R3 is selected from the group consisting of H and C$_1$-C$_4$ alkyl;

X is S or O or NH or substituted-N, wherein the substituent is selected from the group consisting of $C_1$-$C_8$ alkyl, isopropyl, tert-butyl, saturated or unsaturated monocyclic ring with ring size ranging from 3-7, and unsubstituted or substituted phenyl ring which is optionally substituted with one or more substituents selected from the group consisting of $C_1$-$C_8$ alkyl, $C_1$-$C_8$ alkoxyl, $C_1$-$C_8$ alkylcarbonyl, halogen, hydroxyl, amino, nitro, and cyano; and Y is selected from the group consisting of $C_1$-$C_4$ alkyl.

In one embodiment of the method, R1 is OH, R2 is $CH_3O$, R3 is H, X is NH, and Y is $CH_2$. In exemplary embodiments, the compound is 5-(4-hydroxy-phenyl)-3-oxo-penanoic acid [2-95-methoxy-1H-indole-3-yl)-ethyl]-amide (Formula III).

Formula III

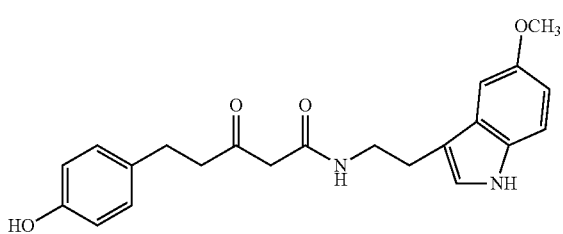

In another embodiment, R1 is OH, R2 is $CH_3O$, R3 is H, X is NH, and Y is $CH_2$. In exemplary embodiments, the compound is 5-(4-hydroxy-phenyl)-3-oxo-pent-4-enoic acid [2-95-methoxy-1H-indole-3-yl)-ethyl]-amide (Formula IV).

Formula IV

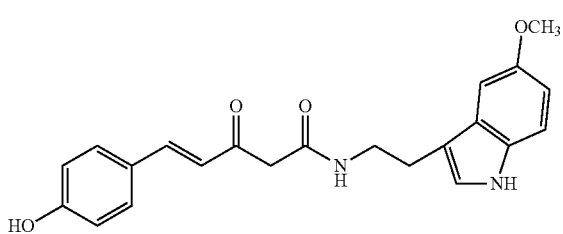

BRIEF DESCRIPTION OF THE DRAWINGS

FIG. 5A-D. Mechanistic studies of 5 and 7. A. MC65 cells were treated with indicated compounds at indicated concentrations for 24 h immediately after the removal of TC. Lysates from cultures were analyzed by Western blotting using 6E10 antibody. The image represents the results from one of three independent experiments. B. Aβ42 was added to solutions of 1 and 7 at indicated concentrations for 48 h. Thioflavin T (ThT) was then added and fluorescence intensity was analyzed at 446 nm (excitation) and 490 nm (emission). Data were presented as a mean percentage of fluorescence intensity (n=3). Error bars represent SEM. Aβ42 were incubated with a solution of 7 in a 1:1 ratio for 24 h. Aggregate morphology of (C) Aβ42 fibrils and (D) Aβ42 oligomers was visualized by AFM.

FIG. 8A-D. AM24 (7) (50 mg/kg) oral gavage treatment in 4 month-old APP/PS1 transgenic animals during 12 weeks. Immunochemistry was performed using anti-Aβ 1-16 Clone 82E1 (1/1000, Mouse) in (A) control and (B) AM24-treated mice. Percent area of (C) Cortex (Cx) and (D) Cortex plus Hippocampus (CxHp) was measured. Statistical analysis was performed by T test *p<0.05. Experiment was assessed with APP/PS1-saline (n=4) and APP/PS1-AM24 (n=7) mice. Scale bar represents 500 µm.

Clone 82E1 (1/1000, Mouse) in (A) control and (B) AM24-treated mice. (C) Percent area Hippocampus (Hp) was measured. Experiment was assessed with APP/PS1-saline (n=4) and APP/PS1-AM24 (n=7) mice. Statistical analysis was performed by T test, no differences were detected. Scale bar represents 200 μm.

FIG. 10A-E. AM24 (7) (50 mg/kg) oral gavage treatment during 12 weeks in 4 month-old APP/PS1 transgenic animals. Immunochemistry in (A) control and (B) AM24-treated mice and (C) Western Blot were performed using anti-GFAP (1/250 and 1/2000 respectively, Rabbit). (D) Band Intensity was compared with saline treated APP/PS1 mice. (E) Percent area Hippocampus (Hp) was measured. Experiment was assessed with APP/PS1-saline (n=4) and APP/PS1-AM24 (n=7) mice. Statistical analysis was performed by T test, no differences were detected. Scale bar represents 200 μm.

Figure 11A:
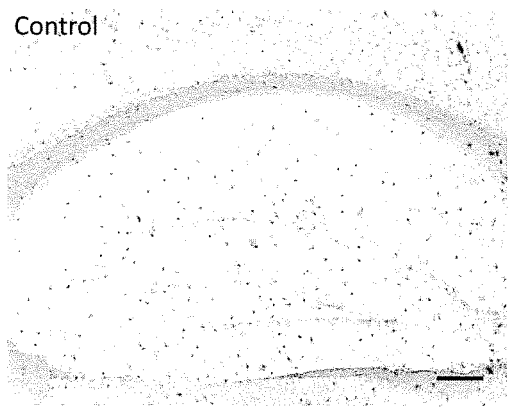
Figure 11B:
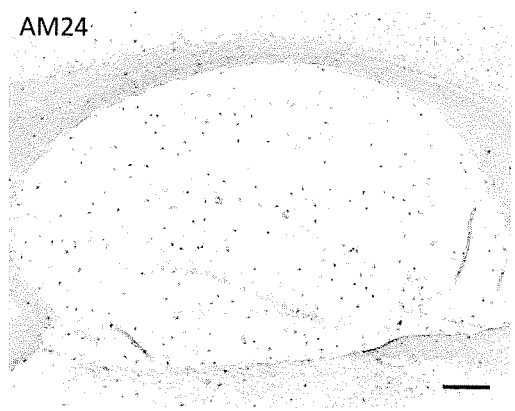
Figure 11C:
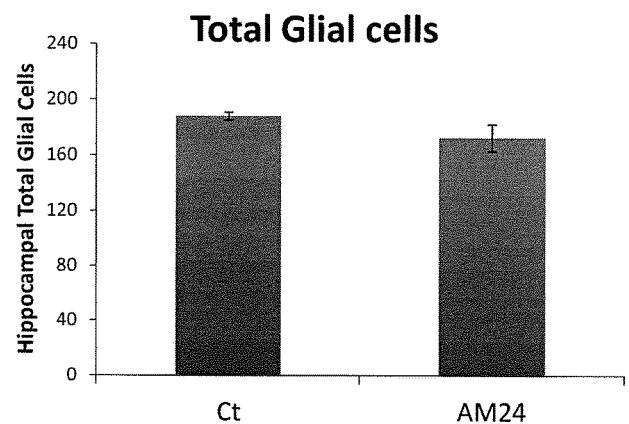

FIG. 11A-C. AM24 (7) (50 mg/kg) oral gavage treatment during 12 weeks in 4 month-old APP/PS1 transgenic animals. Immunochemistry was performed using anti-IBA-1 (1/250, Rabbit) in (A) control and (B) AM24-treated mice. (C) Total number of microglia in Hippocampus (Hp) was counted. Experiment was assessed with APP/PS1-saline (n=4) and APP/PS1-AM24 (n=7) mice. Statistical analysis was performed by T test *p<0.05. Scale bar represents 200 μm.

Figure 12A:
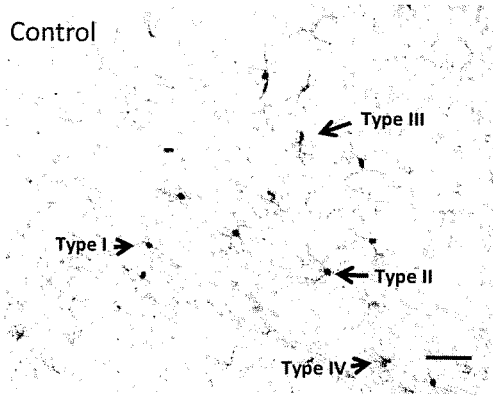
Figure 12B:
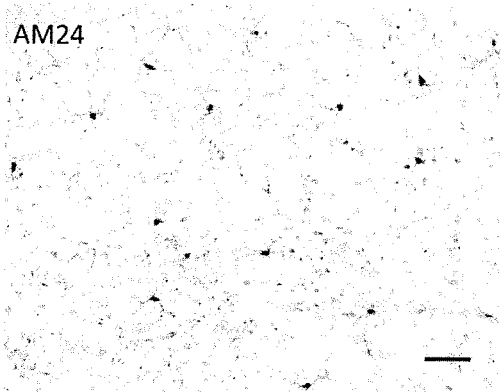
Figure 12C:
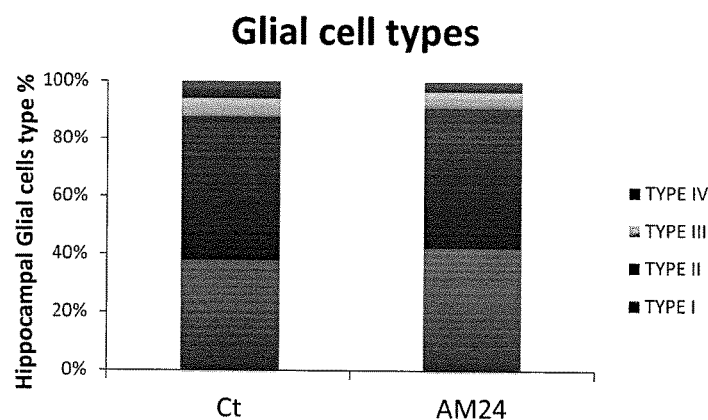

FIG. 12A-C. AM24 (7) (50 mg/kg) oral gavage treatment during 12 weeks in 4 month-old APP/PS1 transgenic animals. Immunochemistry was performed using anti-IBA-1 (1/250, Rabbit) in (A) control and (B) AM24-treated mice. (C) Percentage of different microglial types (activation state) in Hippocampus (Hp) was represented. Pictures show a representative detail microglia image. Experiment was assessed with APP/PS1-saline (n=4) and APP/PS1-AM24 (n=7) mice. Scale bar represents 50 μm. Glial Cell Classification: Type I; Non-activated state cells. Without arms and circular shape. Type II: Low activation state cells. 2-3 arms per cell, a circular-star shape. Type III: Moderate activation state cells. 4-5 arms or more per cell and star-shaped. Type IV; Heavy activation state cells. Bigger cell body, 5 or more arms and strongly star-shaped.

Figures 13A, 13B:
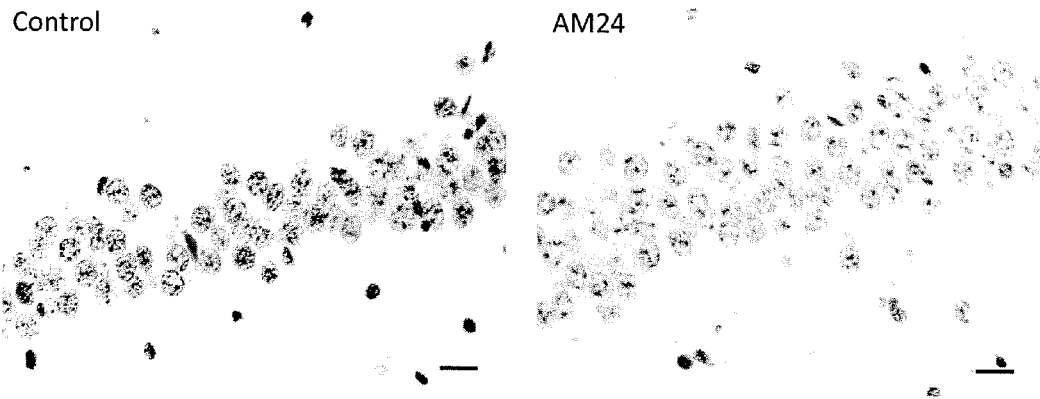
Figure 13C:
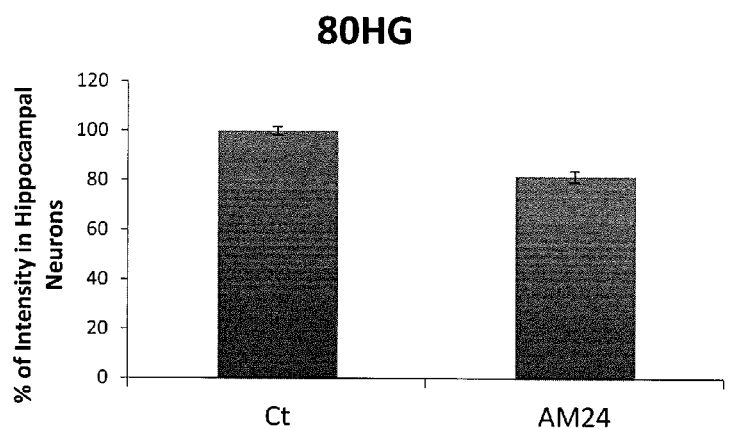

FIG. 13A-C. AM24 (7) (50 mg/kg) oral gavage treatment in 4 month-old APP/PS1 transgenic animals during 12 weeks. Immunochemistry was performed using anti-8OHG (1/750, Mouse) stress marker in (A) control and (B) AM24-treated mice. (C) Intensity of Neuronal DNA damage in CA1, CA2, CA3 was measured. Experiment was assessed with APP/PS1-saline (n=4) and APP/PS1-AM24 (n=7) mice. Statistical analysis was performed by T test **p<0.01. Scale bar represents 20 μm.

Figure 14A:
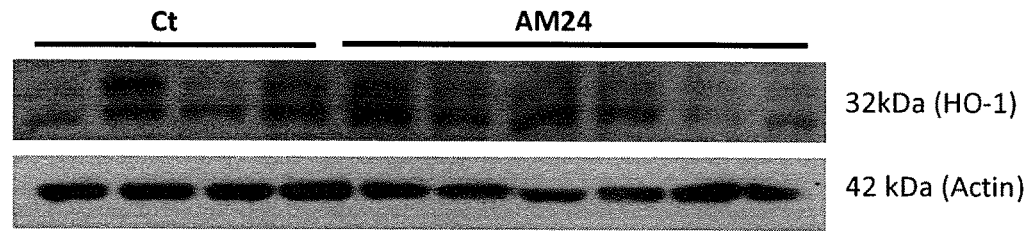
Figure 14B:
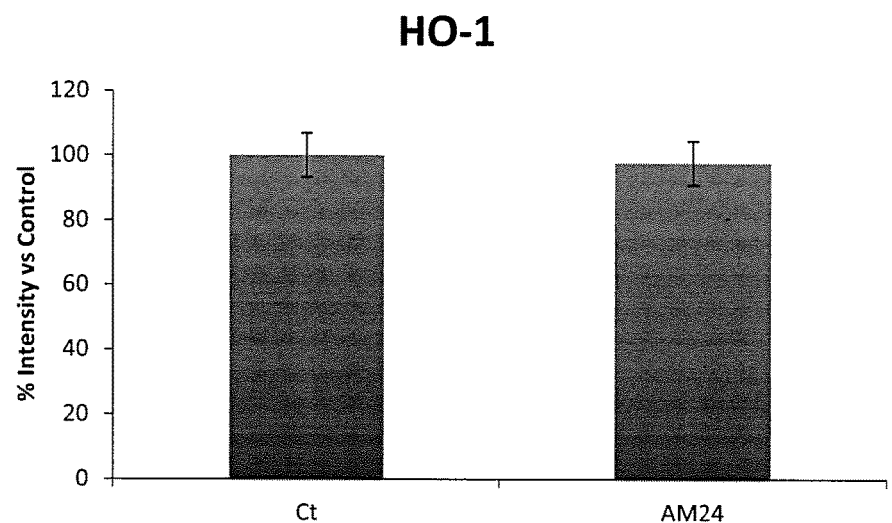

FIG. 14A-B. AM24 (7) (50 mg/kg) oral gavage treatment in 4 month-old APP/PS1 transgenic animals during 12 weeks. (A) Western-blot was performed using anti-HO-1 (1/1000, Rabbit) stress marker. (B) Band Intensity was compared with saline treated APP/PS1 mice. Experiment was assessed with APP/PS1-saline (n=4) and APP/PS1-AM24 (n=7) mice.

Figure 15A:
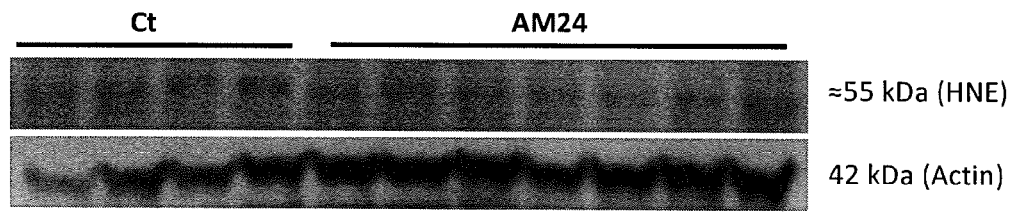
Figure 15B:
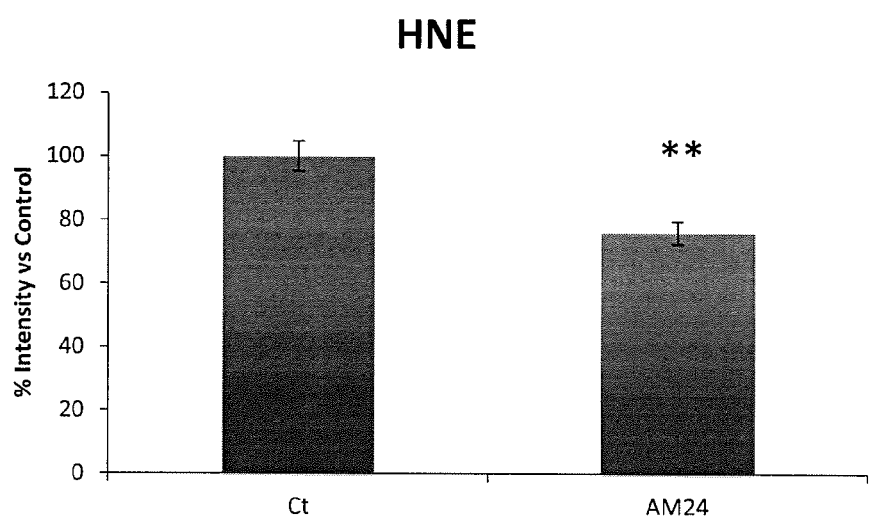

FIG. 15A-B. AM24 (7) (50 mg/kg) oral gavage treatment in 4 month-old APP/PS1 transgenic animals during 12 weeks. (A) Western-blot was performed using anti-HNE (1/2000, Rabbit) stress marker. (B) Band Intensity was compared with saline treated APP/PS1 mice. Experiment was assessed with APP/PS1-saline (n=4) and APP/PS1-AM24 (n=7) mice. Statistical analysis was performed by T test ** p<0.01.

Figure 16A:
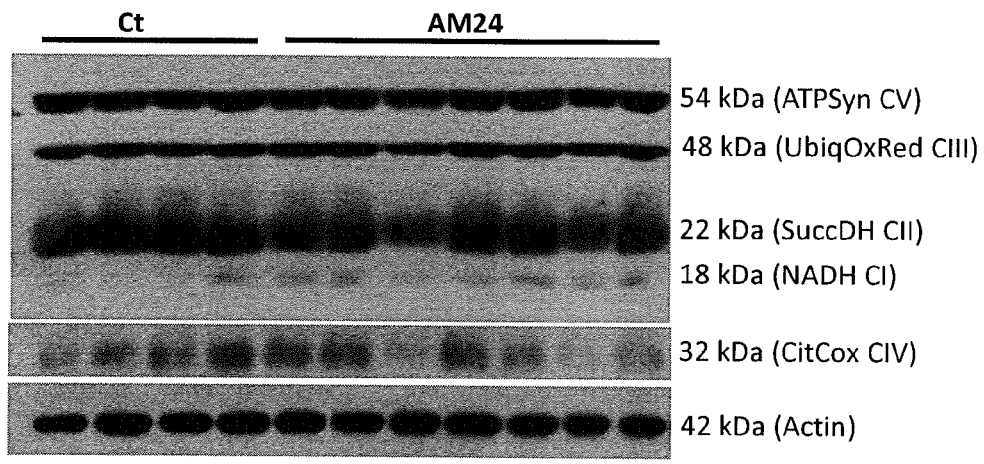
Figure 16B:
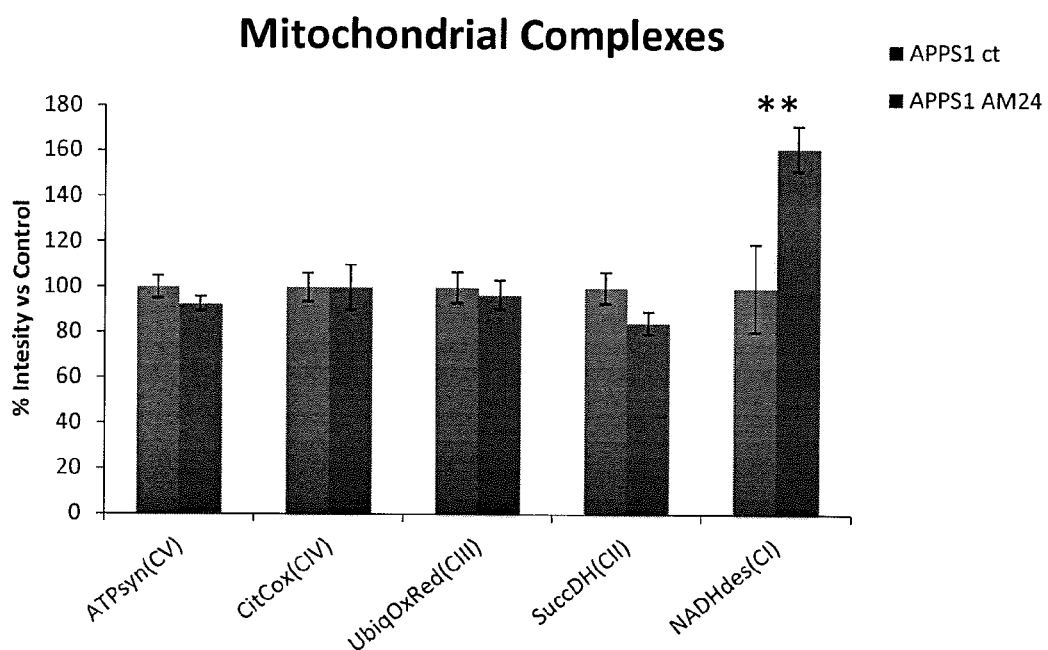

FIG. 16A-B. AM24 (50 mg/kg) oral gavage treatment in 4 month-old APP/PS1 transgenic animals during 12 weeks. (A) Mitochondrial complex Western-blot was performed using OXPhOS cocktail antibody (1/2000, Mouse) to measure I, II, III and V Complex, and MTCO CIV for complex IV (1/2000, Mouse). (B) Band Intensity was compared with saline treated APP/PS1 mice. Experiment was assessed with APP/PS1-saline (n=4) and APP/PS1-AM24 (n=7) mice. Statistical analysis was performed by T test **p<0.01.

Figure 17:
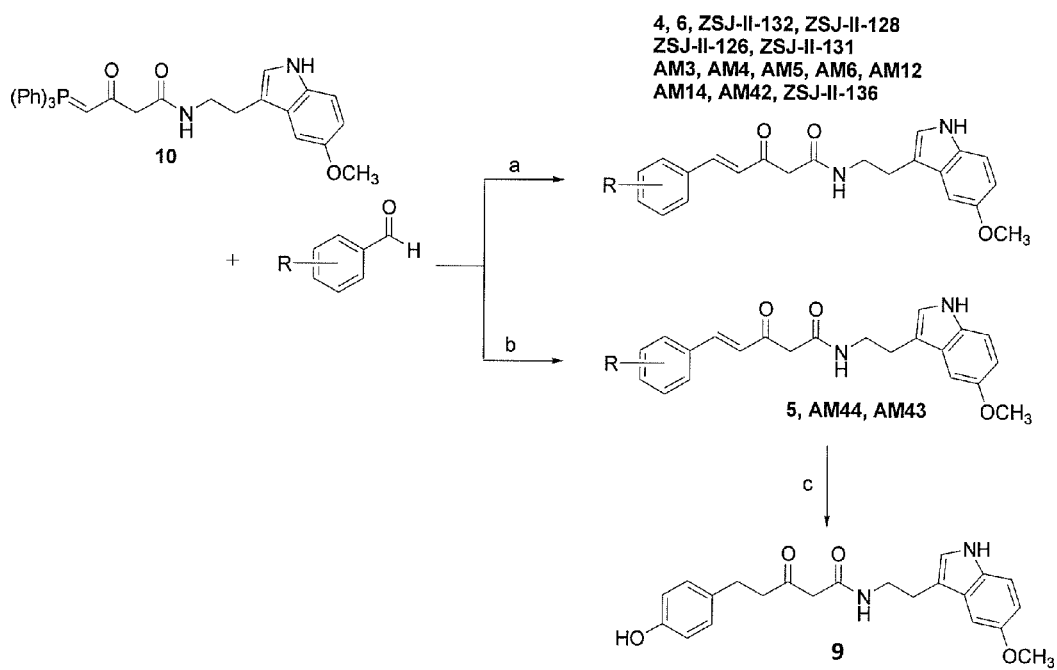

FIG. 17. Synthesis scheme. Synthesis of the designed analogs was achieved with the following the conditions as labeled in the figure (a) NaH, DMPU/THF (1:1.2); (b) DMSO/H2O (5:1); (c) H2, Pd/C, MeOH.

Figure 18:
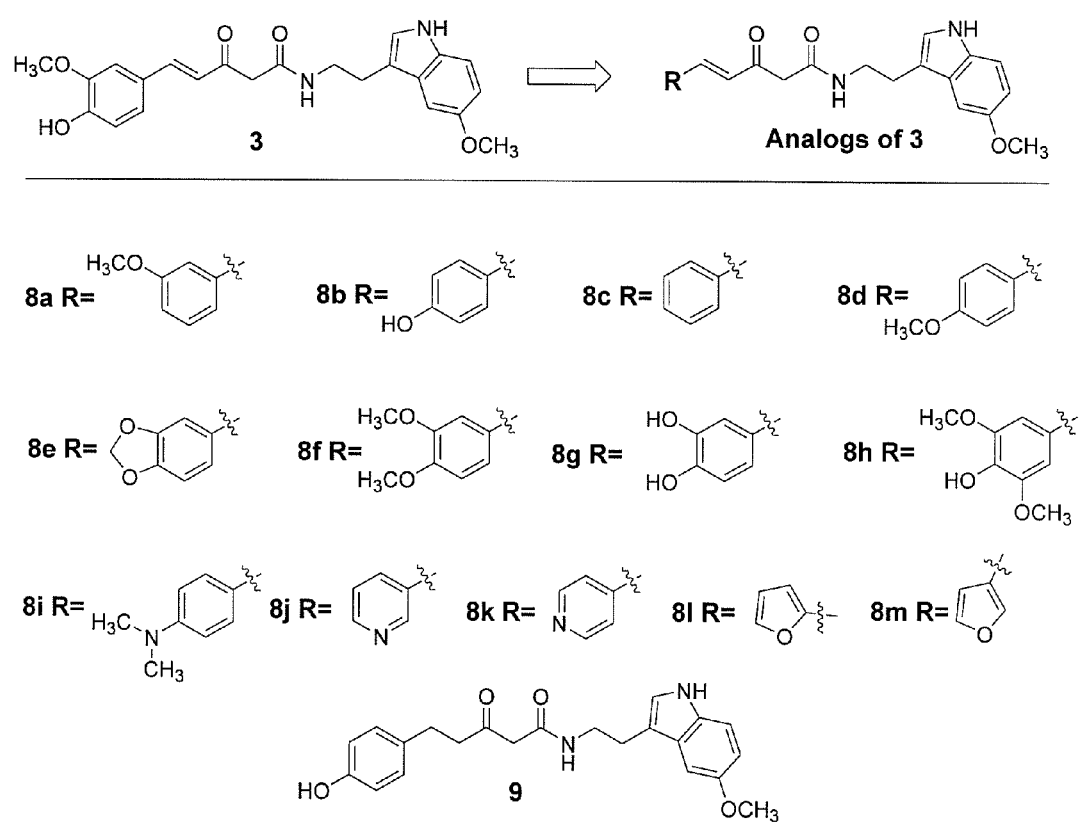

FIG. 18. Rational design of analogs of 3.

FIG. 19A-B. Neuroprotective activities of analogs of 3 in MC65 cells. A. MC65 cells were treated with indicated compounds at 0.3 μM under +TC or –TC conditions for 72 h. Cell viability was assessed by MTT assay. Data were expressed as mean percentage viability (n=4) with parallel +TC cultures set at 100% viability. Error bars represent SEM. B. MC65 cells were treated with 8b or 9 at indicated concentrations under –TC conditions for 72 h. Cell viability was assessed by MTT assay. Data were expressed as mean percentage viability (n=3) with parallel +TC cultures set at 100% viability. Error bars represent SEM.

FIG. 20A-J. Example compounds of the claimed invention. (A) generalized formula of a compound of the claimed invention. (B-H) Formulas of example compounds of the invention containing varied constituents at positions R, R2, R3, X, and Y.

DETAILED DESCRIPTION

Embodiments of the invention provide hybrid compounds of curcumin and melatonin that are useful for the treatment and/or prevention of neurodegenerative disorders. In exemplary embodiments, the disorder is Alzheimer's disease (AD).

Embodiments of the invention provide a compound having the general formula:

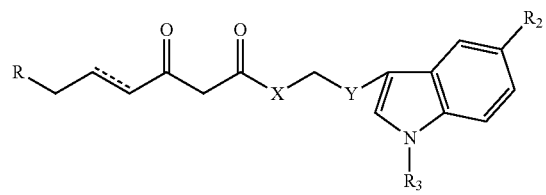

wherein

R is a substituted or unsubstituted aromatic or heteroaromatic group;

R2 is selected from the group consisting of H, OH, $NH_2$, $NO_2$ and $C_1$-$C_8$ alkoxyl;

R3 is selected from the group consisting of H and $C_1$-$C_4$ alkyl;

X is S or O or NH or substituted-N, wherein the substituent is selected from the group consisting of $C_1$-$C_8$ alkyl, isopropyl, tert-butyl, saturated or unsaturated monocyclic ring with ring size ranging from 3-7, and unsubstituted or substituted phenyl ring which is optionally substituted with one or more substituents selected from the group consisting of $C_1$-$C_8$ alkyl, $C_1$-$C_8$ alkoxyl, $C_1$-$C_8$ alkylcarbonyl, halogen, hydroxyl, amino, nitro, and cyano; and Y is selected from the group consisting of $C_1$-$C_4$ alkyl.

In exemplary embodiments, the aromatic or heteroaromatic group is substituted with a hydroxyl or a substituted or unsubstituted amino group. In some embodiments, the aromatic or heteroaromatic group is further substituted with a substituent selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano.

In other embodiments, the substituted or unsubstituted aromatic or heteroaromatic group is a substituted or unsubstituted heteroamic group which includes an oxygen or a nitrogen as the heteroatom. In some embodiments, the aromatic or heteroaromatic group is further substituted with a substituent selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano.

One aspect of the invention provides hybrid compounds with the following formulas: Formula I and Formula II:

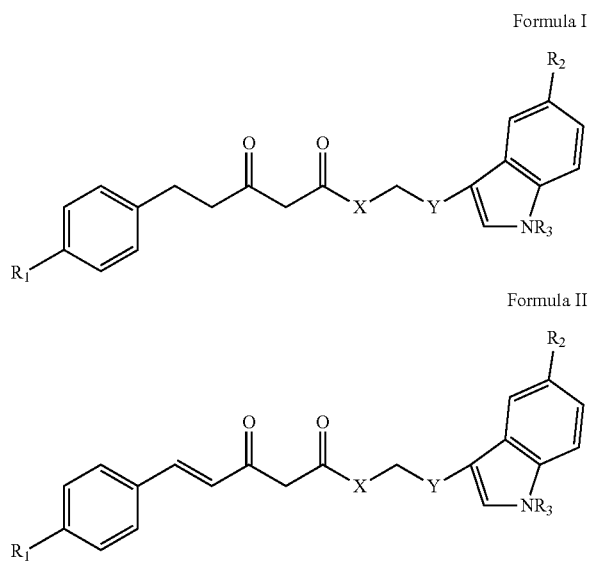

Formula I

Formula II

In Formula I,

R1 is selected from the group consisting of: H, OH and $NH_2$ and substituted-N wherein the substituent is selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano;

R2 is selected from the group consisting of H, OH, $NH_2$, $NO_2$ and $C_1$-$C_8$ alkoxyl;

R3 is selected from the group consisting of H and $C_1$-$C_4$ alkyl;

X is S or O or NH or substituted-N, wherein the substituent is selected from the group consisting of $C_1$-$C_8$ alkyl, isopropyl, tert-butyl, saturated or unsaturated monocyclic ring with ring size ranging from 3-7, and unsubstituted or substituted phenyl ring which is optionally substituted with one or more substituents selected from the group consisting of $C_1$-$C_8$ alkyl, $C_1$-$C_8$ alkoxyl, $C_1$-$C_8$ alkylcarbonyl, halogen, hydroxyl, amino, nitro, and cyano; and Y is selected from the group consisting of $C_1$-$C_4$ alkyl.
In Formula II, R1 is selected from the group consisting of: H, OH and $NH_2$ and substituted-N wherein the substituent is selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano;

R2 is selected from the group consisting of H, OH, $NH_2$, $NO_2$ and $C_1$-$C_8$ alkoxyl;

R3 is selected from the group consisting of H and $C_1$-$C_4$ alkyl;

X is S or O or NH or substituted-N, wherein the substituent is selected from the group consisting of $C_1$-$C_8$ alkyl, isopropyl, tert-butyl, saturated or unsaturated monocyclic ring with ring size ranging from 3-7, and unsubstituted or substituted phenyl ring which is optionally substituted with one or more substituents selected from the group consisting of $C_1$-$C_8$ alkyl, $C_1$-$C_8$ alkoxyl, $C_1$-$C_8$ alkylcarbonyl, halogen, hydroxyl, amino, nitro, and cyano; and Y is selected from the group consisting of $C_1$-$C_4$ alkyl.

A generalized formula of the compound of the invention is shown in FIG. 20A. Exemplary R1, R2, R3, X, and Y constituents are shown in FIGS. 20B-J. All of these compounds can be synthesized substantially as described in the Examples below. The studies described in the Examples below demonstrate that certain compounds have more functional activity in the methods of the claimed invention (for example, as a neuroprotectant) than other compounds, however, the non-functional compounds may be functional in the methods of the claimed invention upon modification of conditions such as dosage. Compounds of the invention may also be synthesized as a prodrug through an ester linkage to a carrier molecule. When the prodrug is administered to a subject, hydrolysis of the ester linkage releases the bioactive compound.

In some embodiments, the substituents of the compounds described herein may be the same or different and are independently selected from the group consisting of $C_1$-$C_8$ alkyl, $C_1$-$C_8$ alkoxyl, $C_1$-$C_8$ alkylcarbonyl, halogen, hydroxyl, amino, nitro, and cyano The term "saturated heterocycle" refers to a saturated monocyclic carbon ring containing at least one heteroatom atom N as part of the ring. The monocyclic ring is fully saturated (i.e. it does not contain any carbon-carbon double or triple bonds). In addition to N bonded directly to Y, one or more additional positions in the ring(s) may be substituted by other heteroatoms, examples of which include, but are not limited to: N, O, S, etc. Exemplary saturated heterocycles that may be used in the practice of the invention include, but are not limited to, morpholine, piperidine, piperazine, pyrrolidine, etc.

The term "saturated or unsaturated monocyclic ring" refers to a fully saturated monocyclic carbon ring (i.e. it does not contain any carbon-carbon double or triple bonds) without or with at least one heteroatom, examples of which include, but are not limited to: N, O, S, etc., as part of the ring. "Unsaturated monocyclic ring" refers to a monocyclic carbon ring containing one or more carbon-carbon or carbon-heteroatom double or triple bonds) with or without at least one heteroatom, examples of which include, but are not limited to: N, O, S, etc., as part of the ring. In some embodiments, the number of carbon atoms in said saturated or unsaturated monocyclic ring with ring size from 3-7 is selected from the group consisting of 3, 4, 5, 6, and 7.

In one embodiment of the invention, the compound of Formula I is the compound 5-(4-hydroxy-phenyl)-3-oxo-penanoic acid [2-95-methoxy-1H-indole-3-yl)-ethyl]-amide as shown in Formula III. Formula III is herein also referred to as AM24 and compound 7. In another embodiment of the invention, the compound of Formula II is 5-(4-hydroxyphenyl)-3-oxo-pent-4-enoic acid [2-95-methoxy-1H-indole-3-yl)-ethyl]-amide as shown in Formula IV. Formula IV is herein also referred to as AM42 and compound 5.

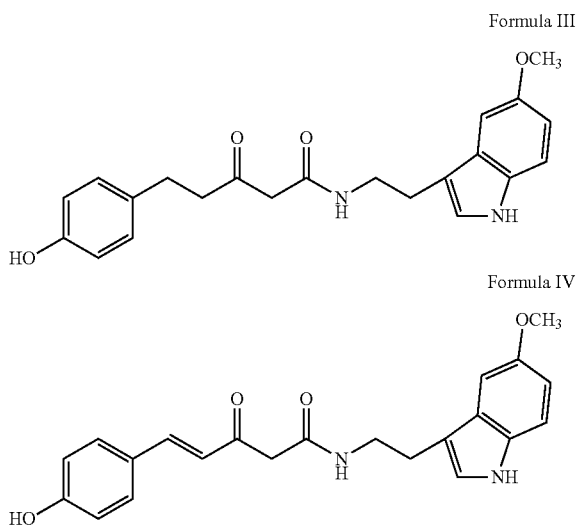

Formula III

Formula IV

The methods of the invention involve identifying subjects or patients who might benefit from receiving therapy for a neurodegenerative disease or disorder, such as AD, through administration of at least one of the hybrid compounds described herein. Such subjects or patients are generally mammals, and usually humans, although this need not always be the case, since veterinary and research related applications of the technology are also contemplated. Generally a suitable subject or patient is identified by a health care professional or professionals using known tests, measurements, or criteria for either already having symptoms of a neurodegenerative disorder, for example AD, or being at risk of developing symptoms of a neurodegenerative disorder such as AD. A suitable treatment protocol is then developed. The methods may also comprise one or more steps related to monitoring the effects or outcome of administration in order to evaluate the treatment protocol and/or to adjust the protocol as required or in a manner that is likely to provide more benefit, e.g. by increasing or decreasing doses of medication, or by changing the particular type of compound that is administered, or by changing the frequency of dosing or the route of administration, etc. While in some cases the improvement or lessening of symptoms (or the prevention of symptoms) that occurs may be complete, e.g. the functioning of the patient returns to or remains normal (as assessed in comparison to suitable control subjects or standardized values obtained therefrom), this need not always be the case. Those of skill in the art will recognize that even a lower level of improvement in symptoms may be highly beneficial to the patient, as may be the slowing of the progression or symptoms of the disease, even if a complete cure does not result.

The term "therapeutically effective amount" refers to an amount of a compound or composition effective to treat a disease or disorder in a subject. In the case of AD or another neurodegenerative disease or disorder, the therapeutically effective amount of the compound or composition may reduce and/or prevent or slow the progression to some extent one or more of the symptoms associated with the disease or disorder.

The methods of the invention involve administering compositions comprising at least one (i.e. one or more) of the hybrid compounds of curcumin and melatonin disclosed herein to a patient in need thereof. The present invention thus also provides compositions which comprise the hybrid compounds as described herein, usually together with a pharmacologically suitable carrier or diluent. In some embodiments, one substantially purified hybrid compound is present in a composition; in other embodiments more than one hybrid compound is present, each hybrid compound being substantially purified prior to being mixed in the composition. The preparation of pharmacologically suitable compositions for use as medicaments is well known to those of skill in the art. Typically, such compositions are prepared either as liquid solutions or suspensions, however solid dry forms such as tablets, pills, powders and the like are also contemplated. The liquid may be an aqueous liquid. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of hybrid compound in the formulations may vary. However, in general, the amount in the formulations will be from about 1% to about 99%.

The hybrid compound compositions (preparations) of the present invention may be administered by any of the many suitable means which are well known to those of skill in the art, including but not limited to: by injection, inhalation, orally, intravaginally, intranasally, by ingestion of a food or product containing the mimic, topically, as eye drops, via sprays, etc. In exemplary embodiments, the mode of administration is orally or by injection. In addition, the compositions may be administered in conjunction with other treatment modalities such as other agents which are used to treat AD or the conditions which cause AD in the patient, examples of which include but are not limited to the administration of anti-depressants and psychoactive drugs, administration of dopamine and similar agents, administration of e.g. donepezil, galantamine, memantine, tacrine, rivastigmine, etc.

The amount of hybrid compound that is administered is generally in the range of from about 1 to about 20 mg/kg, and preferably in the range of from about 5 to about 10 mg/kg, although as one of skill in the art will recognize, the precise amount may vary depending on one or more attributes of the drug recipient, including but not limited to: weight, overall health, gender, age, nationality, genetic history, other conditions being treated, etc.

The hybrid compounds of the invention may be used to treat or prevent the symptoms that occur as a result of the formation of Aβ oligomers and/or aggregation of such oligomers in brain tissue. Any disease or condition that results from the abnormal production and/or accumulation of Aβ oligomers may be treated using the compounds of the invention. Such diseases or conditions and symptoms thereof are usually termed or associated with Alzheimer's disease (AD). In some embodiments the compounds described herein are used prophylactically, e.g. they are administered to persons who have not yet exhibited symptoms of the disease but are deemed to be at risk for developing the disease (e.g. those who are known to have a genetic predisposition for disease development), or simply those who are at risk due to other factors such as aging. The compounds may also be administered to individuals who are thought or deemed to be exhibiting early signs of disease or to be in early stages of disease. The compounds may also be administered to individuals who are known to have and who definitely exhibit symptoms of disease. Administration of the compounds described herein may prevent disease symptoms, may slow the progression of disease, and/or may reverse symptoms. Those of skill in the art will recognize that, while complete remission of disease may be desirable, great benefit may also accrue if partial remission or slowing of disease progress is achieved.

Other embodiments of the invention include the treatment of diseases or disorders associated with neurodegeneration. These methods comprise the step of administering a therapeutically effective amount of at least one of the compounds of formula (I) or formula (II) or a composition thereof to a patient in need thereof to treat or prevent neurodegeneration. Examples of such disease or disorders include but are not limited to Parkinson's disease, Huntington's disease, ALS, and prion disease.

Before exemplary embodiments of the present invention are described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

The invention is further described by the following non-limiting examples which further illustrate the invention, and are not intended, nor should they be interpreted to, limit the scope of the invention.

Example 1

5-(4-hydroxy-phenyl)-3-oxo-pentanoic acid [2-(5-methoxy-1H-indol-3-yl)-ethyl]-amide as a Neuroprotectant for Alzheimer's Disease by Hybridization of Curcumin and Melatonin Summary In an effort to develop effective neuroprotectants as treatments for Alzheimer's disease (AD), hybrid compounds of curcumin and melatonin, two natural products that have been extensively studied in various AD models, were designed, synthesized, and biologically characterized. A lead hybrid compound (7) was discovered to show significant neuroprotection with nM potency ($EC_{50}=27.60\pm9.4$ nM) in MC65 cells, a cellular AD model. Multiple in vitro assay results established that 7 exhibited moderate inhibitory effects on the production of amyloid-β oligomers (AβOs) in MC65 cells, but not on the aggregation of Aβ species. It also exhibited significant antioxidative properties. Further mechanistic studies demonstrated that 7's antioxidant effects correlate well with its neuroprotective potency for MC65 cells, and these effects might be due to its interference with the interactions of AβOs within the mitochondria of MC65 cells. Furthermore, 7 was confirmed to cross the blood-brain barrier (BBB) and deliver a sufficient amount to brain tissue after oral administration. More importantly compound 7 has been shown to reduce the Aβ plaques and oxidative stress in APP/PS1 mouse AD model after oral treatment at 50 mg/kg dose, thus demonstrating its in vivo activities. Compound 7 also affected the mitochondria activity in vivo, which is consistent with our in vitro results.

Materials and Methods

Chemistry:

Reagents and solvents were obtained from commercial suppliers and used as received unless otherwise indicated. All reactions were carried out under inert atmosphere ($N_2$) unless otherwise noted. Reactions were monitored by thin-layer chromatography (TLC) (precoated silica gel 60 $F_{254}$ plates, EMD Chemicals) and visualized with UV light or by treatment with Phosphomolybdic acid (PMA) or ninhydrin.

Flash chromatography was performed on silica gel (200-300 mesh, Fisher Scientific, Inc.) using solvents as indicated. $^1$HNMR and $^{13}$CNMR spectra were routinely recorded on Bruker ARX 400 spectrometer. The NMR solvent used was CDCl$_3$ or DMSO-d6 as indicated. Tetramethylsilane (TMS) was used as the internal standard. HRMS were recorded on PerkinElmer AxION® 2 TOF mass spectrometer. The purity of target compounds was determined by HPLC using Varian® 100-5 C18 250×4.6 mm column with UV detection (280 nm and 360 nm) (50% H$_2$O in acetonitrile and 0.1% trifluoroacetic acid (TFA), and 30-50% H$_2$O in methanol and 0.1% TFA, two solvent systems) to be ≥95%.

Ethyl 4-(triphenylphosphoranylidene)acetoacetate (9)

Triphenylphosphene (14.42 g, 55.25 mmol) was added to a solution of ethyl 4-chloroacetoacetate (8.39 g, 60.76 mmol) in benzene (35 mL) and stirred for 24 h at 55° C. The solution was then cooled to room temperature, and the precipitate was collected by filtration and washed with benzene. The solid precipitate was then dissolved in H$_2$O (10 mL). To this solution a 1 N NaHCO$_3$ solution (10 mL) was added, and the resulting precipitate was collected by filtration, washed with H$_2$O, and then dried under reduced pressure to afford 5 as a white solid (15.31 g, 71%). $^1$H NMR (400 MHz, CDCl$_3$) δ 7.72-7.60 (m, 6H), 7.60-7.50 (m, 3H), 7.45 (m, 6H), 4.19 (q, J=7.13 Hz, 2H), 3.81 (m, 1H), 3.35 (s, 2H), 1.28 (t, J=7.13 Hz, 3H).

Preparation of 10.

Compound 9 (5.04 g, 13.00 mmol) and 5-methoxytryptamine (2.60 g, 13.69 mmol) were added together in xylene (25 mL), and the solution was heated to reflux for 3 h. The solution was then cooled to room temperature and concentrated under reduced pressure. The crude residue was purified by flash chromatography (MeOH/CH$_2$Cl$_2$: 2/98) to give 7 (3.93 g, 57%) as an off-white solid. $^1$H NMR (400 MHz, CDCl$_3$) δ 8.32 (br. s., 1H), 7.89 (br. s., 1H), 7.70-7.51 (m, 9H), 7.50-7.39 (m, 6H), 7.19 (d, J=8.76 Hz, 1H), 7.04 (d, J=2.42 Hz, 1H), 6.93 (d, J=2.06 Hz, 1H), 6.82 (dd, J=8.76, 2.42 Hz, 1H), 3.91 (m, 1H), 3.87 (s, 3H), 3.55 (m, 2H), 3.31 (s, 2H), 2.89 (t, J=7.46 Hz, 2H); $^{13}$C NMR (100 MHz, CDCl$_3$) δ 186.87, 169.47, 153.97, 133.07, 132.97, 132.37, 131.37, 129.06, 128.94, 127.89, 126.63, 125.73, 122.69, 113.28, 112.30, 111.77, 100.46, 100.00, 55.95, 39.45, 25.66.

Procedure A. Preparation of 3.

Compound 10 (0.25 g, 0.47 mmol) was added to a solution of NaH (0.075 g, 1.87 mmol) in DMPU/THF (2 mL/2.2 mL) and cooled to 0° C. for 30 min. To this vanillin (0.085 g, 0.56 mmol) in THF (0.5 mL) was added dropwise. The solution was heated to 40° C. for 3 h. The solution was then cooled to room temperature and stirred overnight. The reaction was then quenched using NH$_4$Cl (0.5 mL). The solvent was removed under reduced pressure and the residual oil was purified by flash chromatography (Hexanes/Acetone: 50/50) to give 3 (0.06 g, 31%) as a light yellow solid. $^1$HNMR (400 MHz, CDCl$_3$) δ 8.03 (s, 1H), 7.56 (d, J=16.04 Hz, 1H), 7.23 (d, J=8.80 Hz, 1H), 7.09 (dd, J=8.28 Hz, 1.84 Hz, 1H), 7.04-6.99 (m, 3H), 6.93 (d, J=8.20 Hz, 1H), 6.85 (dd, J=8.80 Hz, 2.4 Hz, 1H), 6.59 (d, J=16.04 Hz, 1H), 3.92 (s, 3H), 3.86 (s, 3H), 3.63 (q, J=5.76 Hz, 2H), 3.58 (s, 2H), 2.96 (t, J=6.88 Hz, 2H); $^{13}$CNMR (100 MHz, CDCl$_3$) δ 195.31, 165.96, 154.09, 149.00, 147.00, 145.68, 131.56, 127.73, 126.48, 124.18, 123.30, 122.89, 115.00, 112.62, 112.43, 111.95, 109.83, 100.54, 56.03, 55.96, 47.30, 39.79, 25.24. HRMS (m/z) (M-H): calcd. for C$_{23}$H$_{23}$N$_2$O$_5$ 407.1613. found 407.1624.

Preparation of 4.

3-Methoxybenzaldehyde (0.076 g, 0.56 mmol) was reacted with 10 (0.47 mmol) following Procedure A to give 4 (0.06 g, 33%). $^1$H NMR (400 MHz, CDCl$_3$) δ 7.95 (br. s., 1H), 7.71 (d, J=7.53 Hz, 1H), 7.60 (d, J=12.80 Hz, 1H), 7.37 (t, J=8.03 Hz, 1H), 7.32 (t, J=8.00 Hz, 1H), 7.24 (d, J=8.78 Hz, 1H), 7.14 (d, J=8.28 Hz, 1H), 7.04 (s, 1H), 7.03 (br. s., 1H), 6.98 (d, J=1.76 Hz, 1H), 6.85 (dd, J=2.51, 8.78 Hz, 1H), 6.72 (d, J=16.31 Hz, 1H), 3.86 (s, 6H), 3.60-3.67 (m, 4H), 2.97 (t, J=7.03 Hz, 2H); $^{13}$C NMR (100 MHz, CDCl$_3$) δ 195.5, 166.1, 159.9, 159.6, 154.0, 145.3, 135.3, 131.5, 130.0, 129.4, 127.7, 125.8, 122.9, 121.4, 120.1, 117.1, 113.4, 112.3, 111.9, 100.5, 55.9, 55.4, 55.3, 47.1, 39.8, 25.1. HRMS (m/z) (M-H): calcd. for C$_{23}$H$_{23}$N$_2$O$_4$ 391.1663. found 391.1675.

Preparation of 5.

4-Hydroxybenzaldehyde (0.035 g, 0.29 mmol) and 10 (0.25 g, 0.47 mmol) were added together in a DMSO/H$_2$O (5 mL/1 mL) solution, and then heated to 100° C. for 24 h. The reaction was cooled to room temperature, and the product was extracted into EtOAc. The EtOAc layer was washed extensively with H$_2$O and then concentrated under reduced pressure. The residual was twice purified by flash chromatography (1. MeOH/CH$_2$Cl$_2$: 5/95; 2. Hexanes/Acetone: 50/50) to give 5 (0.045 g, 41%). $^1$H NMR (400 MHz, CDCl$_3$) δ 9.01 (br. s., 1H), 8.21 (br. s., 1H), 7.41 (d, J=16.06 Hz, 1H), 7.24 (d, J=8.53 Hz, 2H), 7.09-7.16 (m, 2H), 6.91 (dd, J=2.26, 5.52 Hz, 2H), 6.74 (d, J=8.78 Hz, 2H), 6.69-6.73 (m, 1H), 6.43 (d, J=16.06 Hz, 1H), 3.73 (s, 3H), 3.49 (q, J=6.78 Hz, 2H), 3.45 (s, 2H), 2.84 (t, J=6.78 Hz, 2H); $^{13}$C NMR (100 MHz, CD$_3$COCD$_3$) δ 194.7, 173.2, 168.2, 154.8, 154.8, 144.5, 135.0, 132.9, 131.3, 129.8, 128.5, 124.1, 121.1, 116.6, 113.1, 112.5, 101.2, 55.9, 55.9, 49.3, 40.3, 26.3. HRMS (m/z) (M-H): calcd. for C$_{22}$H$_{21}$N$_2$O$_4$ 377.1507. found 377.1521.

Preparation of 6.

Benzaldehyde (0.060 g, 0.56 mmol) was reacted with 10 (0.25 g, 0.47 mmol) following Procedure A to give 6 (0.05 g, 29%). $^1$H NMR (400 MHz, CDCl$_3$) δ 8.15 (br. s., 1H), 7.59 (d, J=16.06 Hz, 1H), 7.51 (dd, J=1.80, 7.60 Hz, 2H), 7.29-7.45 (m, 3H), 7.21 (d, J=8.78 Hz, 1H), 7.08 (br. s., 1H), 7.02-7.04 (m, 1H), 7.00 (d, J=2.01 Hz, 1H), 6.84 (dd, J=2.51, 8.78 Hz, 1H), 6.71 (d, J=16.06 Hz, 1H), 3.84 (s, 3H), 3.61 (q, J=6.80 Hz, 2H), 3.57 (s, 2H), 2.94 (t, J=6.80 Hz, 2H); $^{13}$C NMR (100 MHz, CDCl$_3$) δ 195.5, 165.6, 154.1, 145.3, 134.0, 131.5, 131.2, 129.1, 128.8, 128.7, 127.7, 127.4, 125.7, 122.9, 112.7, 112.5, 112.0, 100.5, 56.0, 47.4, 39.8, 25.2. HRMS (m/z) (M-H): calcd. for C$_{22}$H$_{21}$N$_2$O$_3$ 361.1558. found 361.1570.

Preparation of 7.

Compound 5 (0.500 g, 1.32 mmol) was dissolved in MeOH (30 mL) under N$_2$. To this Pd/C (0.050 g) was added. The solution was then stirred under H$_2$ at normal pressure overnight. The solution was then filtered to remove Pd/C, and the filtrate was concentrated under reduced pressure. The residue was purified by flash chromatography (MeOH/CH$_2$Cl$_2$: 2/98) to give 7 (0.360 g, 72%). $^1$H NMR (400 MHz, CDCl$_3$) δ 8.37 (br. s., 1H), 7.75 (br. s., 1H), 7.22 (d, J=8.78 Hz, 1H), 7.01 (d, J=2.26 Hz, 1H), 6.91-6.98 (m, 4H), 6.83 (dd, J=2.26, 8.78 Hz, 1H), 6.74 (d, J=8.28 Hz, 2H), 3.83 (s, 3H), 3.55 (q, J=6.61 Hz, 2H), 3.25 (s, 2H), 2.90 (t, J=6.78 Hz, 2H), 2.67-2.78 (m, 4H); $^{13}$C NMR (100 MHz, CDCl$_3$) δ 205.8, 165.8, 155.0, 153.9, 131.5, 131.3, 129.2, 127.6, 123.0, 115.5, 112.2, 112.0, 100.5, 55.9, 49.3, 45.2, 39.7, 28.5, 25.0. HRMS (m/z) (M-H): calcd. for $C_{22}H_{23}N_2O_4$ 379.1663. found 379.1665.

Biological Assays:

Aβ42 was obtained from American Peptide, Inc. (Sunnyvale, Calif.). 6E10 antibody was obtained from Signet (Dedham, Mass.). MC65 cells were cultured in Dulbecco's Modified Eagle's Medium (DMEM) (Life Technologies, Inc., Grand Island, N.Y.) supplemented with 10% of heat-inactivated fetal bovine serum (FBS) (Hyclone, Logan, Utah), 1% Penicillin/Streptomycin (P/S) (Invitrogen), 1 μg/mL Tetracycline (TC) (Sigma Aldrich, St. Louis, Mo.), and 0.2 mg/mL G418 (Invitrogen). HT22 mouse hippocampal cells were cultured in DMEM supplemented with 10% FBS and 1% P/S. All cells were maintained at 37° C. in a fully humidified atmosphere containing 5% $CO_2$. CD-1 male mice were purchased from Harlan Laboratories (Frederich, Md.). All experiments involving animals were carried out in strict accordance with the recommendations in the Guidelines and Regulations of Institutional Animal Care and Use Committee (IACUC) of the Virginia Commonwealth University (VCU). The protocol was approved by the Committee on the Ethics of Animal Experiments of VCU (IACUC Number: AD20114).

Neuroprotection Assay in MC65 Cells.

MC65 cells were washed twice with PBS, resuspended in Opti-MEM, and seeded in 96-well plates ($4\times10^4$ cells/well). Indicated compounds were then added, and cells were incubated at 37° C. under +TC or -TC conditions for 72 h. Then, 10 μL of MTT (5 mg/mL in PBS) were added and the cells were incubated for another 4 h. Cell medium was then removed, and the remaining formazan crystals produced by the cellular reduction of MTT were dissolved in DMSO. Absorbance at 570 nm was immediately recorded using a FlexStation® 3 plate reader (Molecular Devices, CA).

ROS Production Assay in MC65 Cells.

MC65 cells were washed twice with PBS, resuspended in Opti-MEM®, and seeded in 6-well plates ($8\times10^5$ cells/well). Indicated compounds were then added, and cells were incubated at 37° C. under +TC and -TC conditions for 48 h. Cells were harvested, washed twice with cold PBS, then suspended in PBS and incubated with DCFH-DA (25 μM) in dark for 1 h. Fluorescence was analyzed by flow cytometry using a Millipore Guava® easyCyte flow cytometer.

Western Blot Assay.

MC65 cells ($4\times10^5$ cells/mL) were treated with indicated compounds for 30 h and then were lysed by sonication in a Tricine buffer solution and boiled for 5 min. Protein samples were collected from the supernatant after centrifugation of the samples at 12,800×g for 5 min, and then quantified using the Bradford method. Equal amounts of protein (20.0 μg) were separated by SDS-PAGE on a gel (Bio-Rad) and transferred onto a PVDF membrane (Bio-Rad). The blots were blocked with 5% milk in TBS-Tween 20 (0.1%) solution at room temperature for 1 h and then probed with the 6E10 antibody overnight at 4° C. The blots were washed twice in TB S-Tween 20 for 15 min, and then incubated with a 1:1000 dilution of horseradish peroxidase-conjugated secondary antibody in a 5% milk/PBS-Tween 20 solution at room temperature for 1 h. After washing twice in TBS-Tween 20 for 15 min, the proteins were visualized by a Western Blot Chemiluminescence Reagent (Thermo Fischer Scientific, Waltham, Mass.). The blots were also probed with antibodies against α-tubulin to ensure equal loading of proteins.

Thioflavin T Assay.

Briefly, 1 μL of each compound solution in DMSO (0.01 μM to 100 μM) was added to corresponding wells in a 96-well plate. Each concentration was prepared in independent triplicates and a solvent control was included. To each well, 9 μL of 25 μM Aβ42 in PBS (pH 7.4) was added, and then plates were incubated in dark at room temperature for 48 h. Next, 200 μL of a 5 μM ThT in 50 mM glycine solution (pH 8.0) was added to each well. Fluorescence was immediately recorded using a FlexStation 3 plate reader (Molecular Devices, CA) at an excitation wavelength of 446 nm and an emission wavelength of 490 nm.

AFM Analysis of 41-42 Fibril and Oligomer Formation.

Aβ42 oligomers and fibrils were prepared based on reported procedures.[43] Indicated compounds were incubated with Aβ42 at a 1:1 ratio for both conditions for 24 h. Samples were loaded on mica, washed extensively with water, and dried overnight at room temperature before AFM analysis. The morphology of the Aβ42 aggregates was assessed using an atomic force microscope (Dimension Icon, Bruker) operating in tapping mode in air. The scan rate was varied between 1 Hz and 0.5 Hz depending on the tracking quality. The silicon tips (Bruker mpp2100-100) have a sharpness of less than 5 nm and a force constant between 3 and 5 N/m along with a resonant frequency rated between 60-90 Hz. All images were taken with 512 points per line, with a 1:1 ratio. Images were processed using Nanoscope analysis software version 1.20 and Image-J (from the National Institutes of Health).

Hydrogen Peroxide Toxicity Assay in HT22 Cells.

HT22 cells were seeded in 96-well plates ($4\times10^3$ cells/well) in growth medium and incubated for 24 h at 37° C. The medium was removed and compounds were added at the indicated concentrations in fresh growth medium, and the cells were incubated for another 1 h. $H_2O_2$ was then added at a final concentration of 500 μM, and the plates were then incubated for 24 h. Cell viability was assessed by MTT assay as previously described. Values were expressed as a percentage relative to the negative ($H_2O_2$-free) control.

Rotenone Protection Assay in MC65 Cells.

MC65 cells were seeded in 96-well plates ($4\times10^4$ cells/well) in growth medium and incubated for 24 h at 37° C. The medium was removed and compounds were added at the indicated concentrations in fresh growth medium, and the cells were incubated for another 2 h. Rotenone was then added at a final concentration of 10 μM, and the plates were then incubated for 48 h. Cell viability was assessed by MTT assay.

In Vivo BBB Penetration Experiment.

Briefly, ten week old CD-1 male mice were purchased from Harlan Laboratories (Frederich, Md.). Compound 9 was diluted to a concentration of 15 mg/mL in a solution with 2% DMSO and 10% Cremophor in PBS, and was administered via oral gavage at a final dosage of 50 mg/kg. Two groups of mice (n=6/group) were used to determine the plasma and brain concentrations of the compound at various time-points. Following administration of anesthetic (sodium pentobarbital 150 mg/kg, Sigma Aldrich, Saint Louis, Mo.), blood samples were collected from the inferior vena cava to prepare plasma. Afterwards, the right atrium was removed to allow exsanguination, and the left ventricular apex was cannulated with a 24 G needle and perfused with 30 mL of warm (37° C.) heparinized normal saline solution to enable perfusion of all the organs and complete blood washout. The perfused brains were then collected, rapidly washed in normal saline, blot-dried, and frozen in liquid nitrogen. Brain samples were then analyzed by the LC-MS/MS.

LC-MS/MS Analysis.

For brain samples, half a brain was weighed and diluted with 1.0 mL of acetonitrile and then mixed well. For plasma samples, 0.01 mL of plasma was diluted with 0.99 mL of acetonitrile and then mixed well. After mixing, samples were centrifuged at 15,000 rpm and the supernatant was transferred to a new tube and evaporated to dryness using spin vacuum. The samples were then reconstituted with an 80:20 solution of 1% acetic acid in acetonitrile: 1% acetic acid in water, and a volume of 0.025 mL was then injected into the LC-MS/MS. The LC/MS/MS method employed positive electrospray ionization (ESI) with a selected reaction monitoring (SRM) mode. Compound 9 was monitored using the following SRM transitions: 381→174, 130, and 159. Chromatographic separation was achieved under gradient conditions using a Waters Acquity® UPLC, with a reversed phase column (Gemini 5u C18 110 Å, 100 mm×2.0 mm; 5 um, Phenomenex Inc., Torrance, Calif.) with a mobile phase composition of 1% acetic acid in water (mobile phase A) and 1% acetic acid in acetonitrile (mobile phase B). The initial gradient consisted of 30% B for 1 min, 30% to 95% B from 1 to 3 min, hold for 1 min at 95% B, and then equilibrate at 30% B for 2.5 min. The total run time was 6.5 min. Results were processed using Analyst 1.5.2 software. Absolute recovery, precision and accuracy, and matrix effects experiments produced an efficient method to continue sample analysis. Calibration curves were made with freshly prepared samples and calculated using peak area versus concentration with a linear or quadratic regression. Accuracy fell in the range of 85% to 115%.

Results

Figure 1:
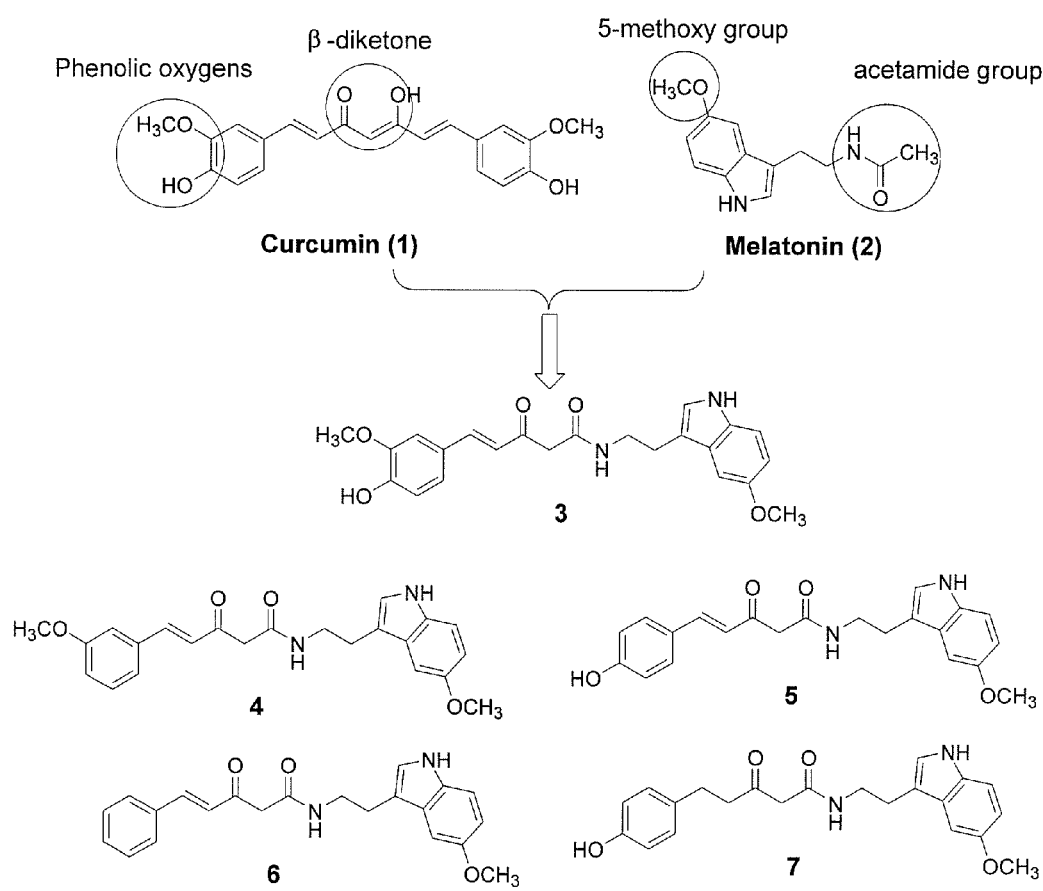
FIG. 1. Chemical structures of curcumin (1), melatonin (2), and rationally designed hybrids 3-7.

The desired hybrids preferably contain the structural features of 1 and 2 that are essential to their pharmacology properties. The phenolic oxygens and the β-diketone moiety of 1 have been demonstrated to be important for its anti-oxidant, anti-inflammatory, and metal chelating properties.[22] The 5-methoxy group and the acetamide moiety of 2 have been shown to be important for its antioxidant and free radical scavenging properties.[13] Therefore, in the newly designed hybrids, it was desired to include all of these structural features. As shown in FIG. 1, we initially designed hybrid 3 to incorporate the β-diketone of 1 and the acetamide moiety of 2 into a β-ketone amide moiety. The indole moiety of 2 was also included to replace one of the phenyl rings of 1. In addition, several congeners of 3 (compounds 4-6) were designed to evaluate the importance of the 4-OH and 3-$CH_3O$ substitutions on the curcumin part of 3, given the fact that structural modifications on the phenyl ring of 1 can significantly affect its biological activities.

Figure 2A:
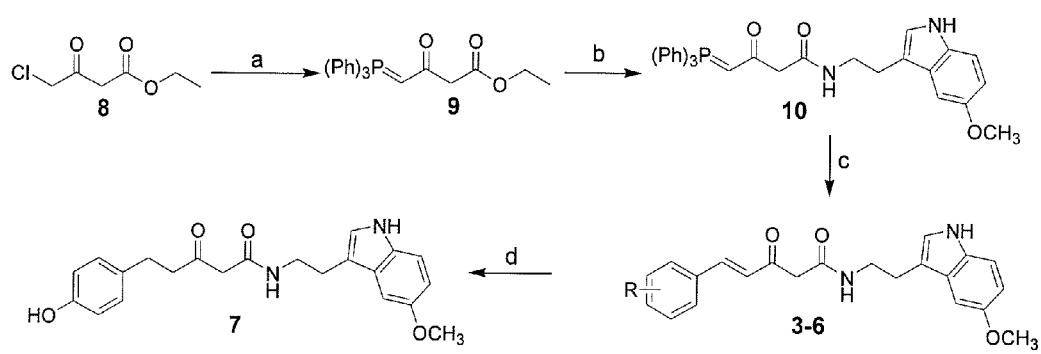
FIG. 2A-B. Synthetic route for the preparation of hybrids 3-7. A. Reagents and conditions: (a) $Ph_3P$, benzene, $\Delta$; (b) 5-methoxy-tryptamine, xylene, $\Delta$; (c) NaH, aldehyde, DMPU/THF (1:1.2), or aldehyde, DMSO/$H_2O$ (5:1), $\Delta$; (d) $H_2$, Pd/C, MeOH. B. Exemplary aromatic groups (position R in FIG. 2A) found in title hybrid compounds FIG. 3. NMR spectrum of 3. The coupling constant (J) of the two vicinal alkene protons is 16 Hz, indicating the trans-product of this structure.
Figure 2B:
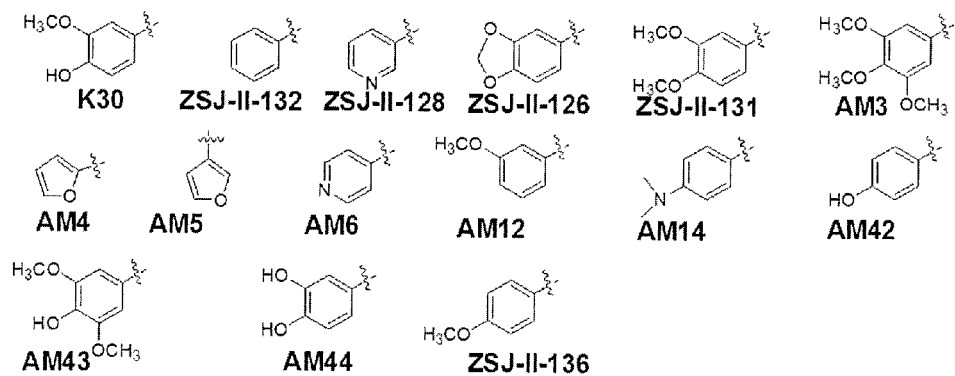
Figure 3:
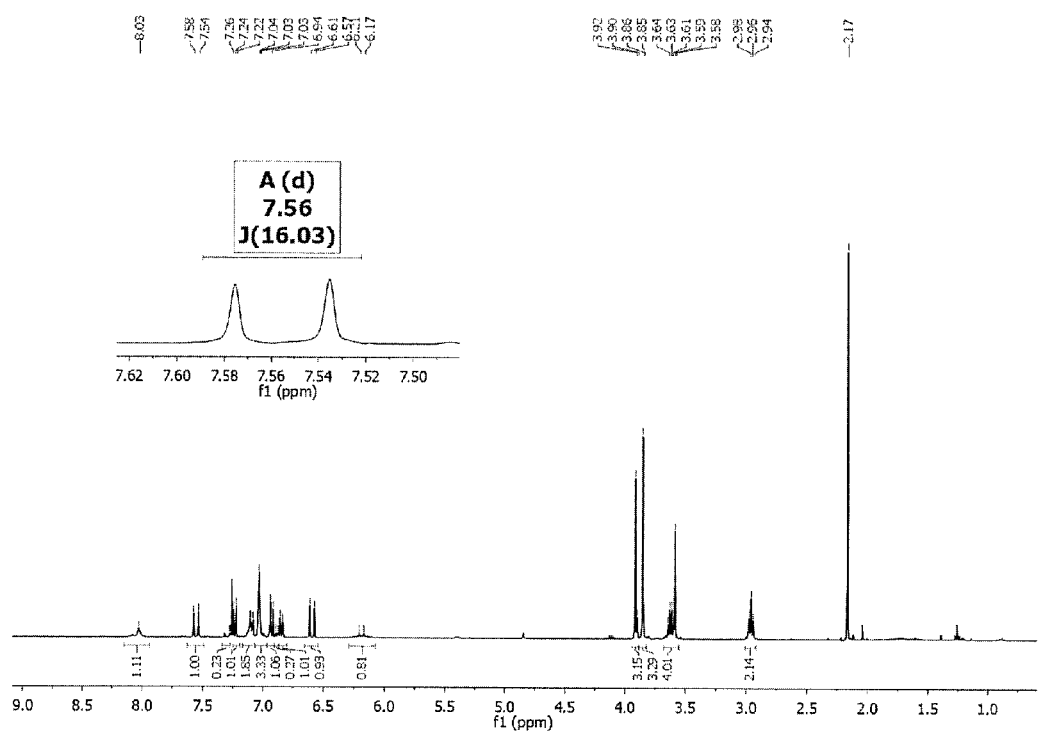

The chemical synthesis of hybrids 3-6 was achieved following the procedures and conditions outlined in FIG. 2A. Briefly, ethyl 4-chloroacetoacetate 8 was reacted with $Ph_3P$ to give the ylide 9 in good yield. Condensation of 9 with 5-methoxy-tryptamine in xylene under refluxing conditions yielded 10, which upon a Wittig reaction with the corresponding aldehyde in DMPU/THF in the presence of NaH, or in $DMSO/H_2O$ under heating conditions finally afforded the designed hybrids 3-6.[23] Interestingly, only the trans-product was obtained under these experimental conditions, which was demonstrated by the coupling constant (J) of the two vicinal alkene protons from 3 being 16.03 Hz (FIG. 3). FIG. 2B illustrates exemplary aromatic groups (position R in FIG. 2A) found in title hybrid compounds.

Figure 4A:
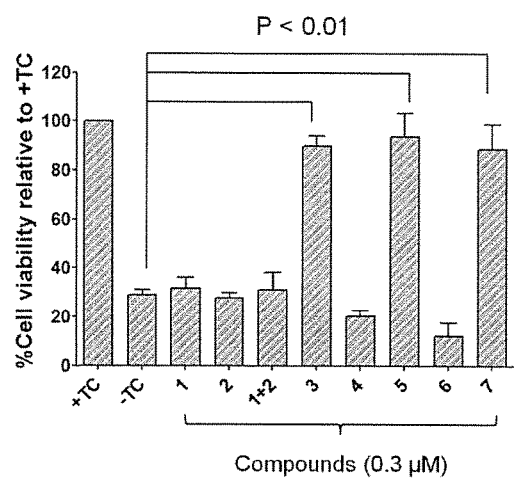
FIG. 4A-B. Neuroprotective effects of designed hybrids. A. MC65 cells were treated with indicated compounds at 0.3 µM under +TC or −TC conditions for 72 h. Cell viability was assessed by MTT assay. Data were expressed as mean percentage viability (n=3) with parallel +TC cultures set at 100% viability. Error bars represent SEM. B. MC65 cells were treated with indicated compounds at indicated concentrations under −TC conditions for 72 h. Cell viability was assessed by MTT assay. Data were expressed as mean percentage viability (n=3) with parallel +TC cultures set at 100% viability. Error bars represent SEM.
Figure 4B:
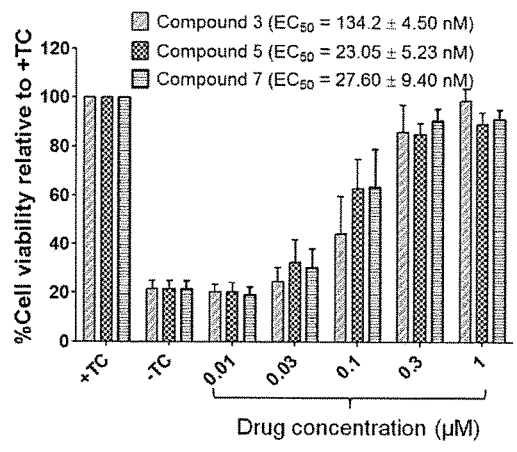

After synthesizing these compounds, their neuroprotective activities were evaluated in MC65 cells, a well-established cellular AD model that is associated with Aβ- and oxidative stress-induced cellular toxicities, under tetracycline removal (−TC) conditions.[24] Initially, a concentration of 0.3 μM was tested in order to establish active lead structures with reasonable potency. Compounds 1 and 2 alone and the combination of 1 and 2 were compared as controls. As shown in FIG. 4A, no neuroprotection was observed in MC65 cells for 1 and 2 alone, as well as the combination of 1 and 2 under −TC conditions at this concentration. These results are consistent with our previously reported results of 1 in MC65 cells.[25, 26] The combination of 1 and 2, and 1 alone showed moderate neuroprotection at much higher concentrations (3 and 10 μM, data not shown). This also indicates that although 2 has been reported to have activity in other cellular models of neurodegenerative disorder, it might not be sufficient to protect MC65 cells under current testing conditions and concentrations. Notably, compound 3 significantly protected MC65 cells from −TC induced cell death (~61% increase in cell viability), which suggests that the combination of essential features of 1 and 2 can provide novel chemical scaffolds with new pharmacology. Removal of 4-OH from 3 as demonstrated by compound 4 led to a complete loss of neuroprotection in MC65 cells, while removal of 3-$CH_3O$ did not affect its biological activity as compound 5 showed significant neuroprotection in MC65 cells. These results clearly indicate that the 4-OH group is essential to the neuroprotective activities of 3. This notion is further supported by the results of the unsubstituted analog 6, which exhibited diminished protections of MC65 cells. Interestingly, 5 can be recognized as the hybrid of 2 and raspberry ketone, another natural product, thus further supporting our hypothesis of the hybrid strategy. To further evaluate the role of the double bond between the phenyl ring and the β-ketone, compound 7 was synthesized (FIG. 2A) and evaluated. Notably, 7 exhibited significant and comparable protection of MC65 cells with 5 (FIG. 4A), suggesting that the double bond and the conjugation system with the phenyl ring is not necessary to produce neuroprotection for these analogs. Further dose-response studies of 3, 5, and 7 established an $EC_{50}$ of 134.2±4.5, 23.05±5.23, and 27.60±9.40 nM, respectively, for their neuroprotection of MC65 cells (FIG. 4B).

The promising and potent protective activities of this novel chemotype in MC65 cells strongly suggest that it may serve as a new template in developing more effective neuroprotectants for AD patients. Therefore, further studies were conducted to obtain preliminary mechanistic data of this hybrid skeleton. This will help facilitate the design and evolution of next generation small molecules. Under −TC conditions, MC65 cells can produce intracellular AβOs that eventually lead to cell death. Therefore, we first evaluated the inhibitory effects of 5 and 7 on the production of AβOs in MC65 cells. As shown in FIG. 5A, both 5 and 7 dose-dependently suppressed the production of AβOs, including tetramers, pentamers, and heptamers. However, the potency of 5 and 7 in suppressing AβOs is significantly lower than their potencies for protecting MC65 cells from −TC induced cytotoxicity (FIG. 4B). This may suggest that the suppression of AβOs only contributes partially, if not at all, to their protection in MC65 cells and may not constitute the major mechanism of action. To further confirm effects on Aβ aggregation, 7's ability to inhibit the formation of Aβ42 fibrils was tested using the thioflavin T (ThT) assay. Compound 1, known to inhibit Aβ fibrillization, was tested as a positive control. As shown in FIG. 4B, 1 inhibited the formation of Aβ42 (25 μm) fibrils by 27.3% at 10 μM, consistent with reported results. However, no significant inhibition was observed for 7 up to 100 μM, thus suggesting that 7 cannot bind to Aβ42 and inhibit its fibrillization.

Atomic force microscopy (AFM) studies of Aβ42 aggregation also confirmed that 7 showed no inhibition on both fibrillization and oligomerization of Aβ42 under current assay conditions (FIG. 5C-D).

Figure 6A:
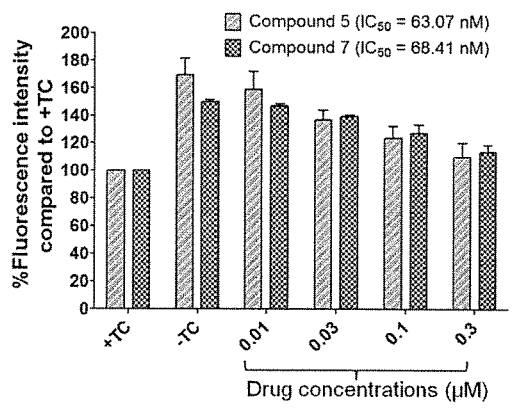
FIG. 6A-C. Antioxidative activity of 5 and 7, and protective activities of known antioxidants. A. MC65 cells were treated with 5 or 7 at indicated concentrations under −TC conditions for 48 h, then DCFH-DA (25 µM) was loaded and fluorescence intensity was analyzed at 485 nm (excitation) and 530 nm (emission). Data were presented as a mean percentage of fluorescence intensity (n=3). Error bars represent SEM. B. MC65 cells were treated with Trolox or NAC at indicated concentrations under −TC conditions for 72 h. Cell viability was assessed by MTT assay. Data were expressed as mean percentage viability (n=3) with parallel +TC cultures set at 100% viability. Error bars represent SEM. C. HT22 cells were treated with Trolox or 7 at indicated concentrations before addition of $H_2O_2$ (500 µM) and incubated for 24 h. Cell viability was assessed by MTT assay. Data were expressed as mean percentage viability (n=3) with parallel $H_2O_2$-free cultures set at 100% viability. Error bars represent SEM.
Figure 6B:
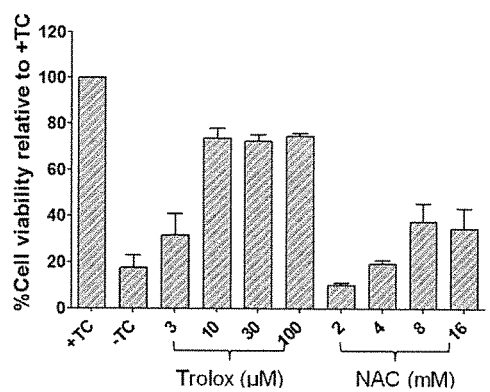

Next, it was investigated as to whether 5 and 7 exhibit antioxidative effects in MC65 cells since oxidative stress has been suggested as one potential contributor to neurotoxicity upon the accumulation of intracellular AβOs. As shown in FIG. 6A, both 5 and 7 dose-dependently suppressed intracellular oxidative stress, with an $IC_{50}$ of ~63 and ~68 nM, respectively, being slightly less than their $EC_{50}$ values from the neuroprotection assays. This may suggest that all of the upstream stimuli/signaling from the production of AβOs channels into oxidative stress that eventually leads to MC65 cell death. To further confirm this notion, known antioxidants, N-acetylcysteine (NAC) and Trolox (6-hydroxy-2,5,7,8-tetramethyl chroman-2-carboxylic acid), were tested for their protection in MC65 cells under the same assay conditions as 7. Notably, like 7, Trolox significantly protected cells from −TC-induced cytotoxicity at concentrations as low as 10 μM. NAC only partially rescued cell viability at 8 and 16 mM concentrations (FIG. 6B), which is consistent with previously reported results.[25] Given the fact that Trolox and NAC have different antioxidative mechanisms, NAC being mainly a hydrogen peroxide scavenger and Trolox, a chain-breaking antioxidant, being particularly effective against lipid peroxidation,[27-29] this may suggest that ROS-induced lipid peroxidation is involved in the death of MC65 cells. Taken together, these results strongly support our notion that oxidative stress is the convergent event after the production of AβOs in MC65 cells that ultimately leads to cell death.

Figure 6C:
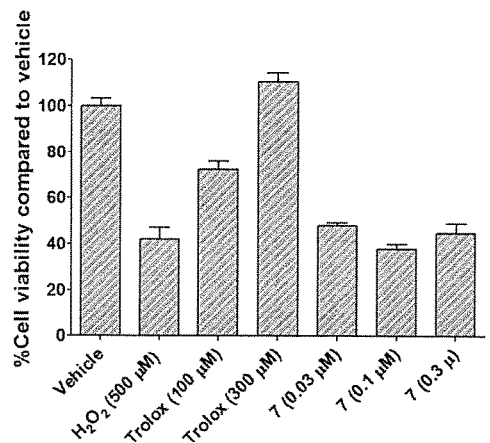

The manifested antioxidative effects of 5 and 7 in MC65 cells could be produced through different mechanisms, for example, the inhibition of AβO production, the interactions of AβO with various partner proteins, or direct antioxidative effects. Therefore, we set out to investigate the possible mechanisms of 7's antioxidative effects. Since it was demonstrated that 7 does not inhibit the aggregation of Aβ and inhibits the production of AβOs, but with a significantly lower potency compared to its neuroprotection potency in MC65 cells, 7's ability to protect HT22 cells, a murine hippocampal line, from $H_2O_2$-induced cell toxicity was tested, another widely used cellular antioxidant model.[30, 31] The results from this assay will help rule out the possibility of 7's direct antioxidative effects. As shown in FIG. 6C, $H_2O_2$ (500 μM) led to significant HT22 cell death (~58%). As expected, the known antioxidant Trolox dose-dependently protected cells from $H_2O_2$-induced cytotoxicity with full rescue at 300 μM. However, no protection was observed for 7 at up to 0.3 μM under the same experimental conditions. Taken together, the results suggest that the effects of 7 observed in MC65 cells are not through direct antioxidation, thus indicating that 7 may be functioning somewhere between the production of AβOs and the accumulation of ROS, for example, the interactions of AβO with partner proteins.

Figure 7A:
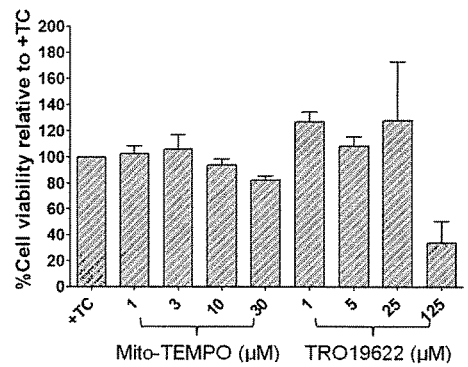
FIG. 7A-D. Effects on viability of TRO19622, Mito-TEMPO and 7 in MC65 cells. A. MC65 cells were treated with Mito-TEMPO or TRO-19622 at indicated concentrations under normal growth conditions (+TC) for 72 h. Cell viability was assessed by MTT assay. Data were expressed as mean percentage viability (n=3) with parallel +TC cultures set at 100% viability. Error bars represent SEM. B. MC65 cells were treated with Mito-TEMPO at indicated concentrations under −TC conditions for 72 h. Cell viability was assessed by MTT assay. Data were expressed as mean percentage viability (n=3) with parallel +TC cultures set at 100% viability. C. MC65 cells were treated with TRO-19622 at indicated concentrations under −TC conditions for 72 h. Cell viability was assessed by MTT assay. Data were expressed as mean percentage viability (n=3) with parallel +TC cultures set at 100% viability. D. MC65 cells were treated with 7 or Mito-TEMPO at indicated concentrations for 2 h before addition of rotenone for 48 h. Cell viability was assessed by MTT assay. Data were expressed as mean percentage viability (n=3) with parallel +TC cultures set at 100% viability.
Figure 7B:
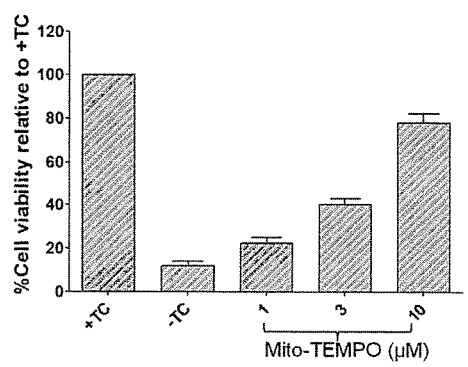
Figure 7C:
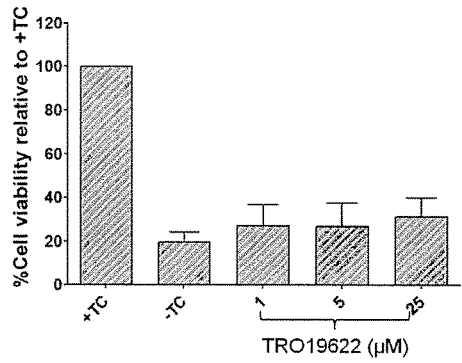
Figure 7D:
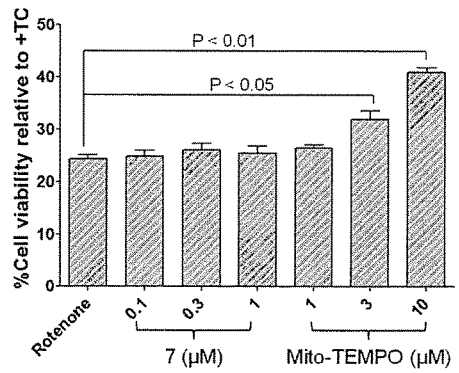

Since mitochondria are the main sites to generate intracellular ROS,[32, 33] it was investigated further as to whether 7 functions in mitochondria to exhibit its antioxidant and neuroprotective activities. To that end, the neuroprotective effects of TRO-19622, a mitochondrial permeability transition pore (mPTP) inhibitor,[34] and Mito-TEMPO, a known mitochondrial ROS (mitoROS) specific scavenger,[35] were tested on MC65 cells from −TC-induced cytotoxicity since mPTP has been reported to be associated with mitochondrial ROS production,[36] and 7 has shown antioxidant effects in MC65 cells. Initially, these two compounds under normal growth conditions (+TC) were tested in MC65 cells to identify concentrations with no cytotoxic effects, thus ruling out any potential biased interpretation of the following assays. As shown in FIG. 7A, Mito-TEMPO did not show toxic effects up to 10 μM and TRO-19622 did not show cytotoxicity up to 25 μM. Therefore, these two concentrations were chosen as maximums for their respective compounds in the following tests. As shown in FIG. 7B, Mito-TEMPO dose-dependently protected MC65 cells from −TC induced cytotoxicity, while TRO-19622 did not show significant protection up to 25 μM (FIG. 7C). Combining these with the results of 7's antioxidant and neuroprotective effects, this may indicate that AβOs, produced upon TC removal, interact with certain mitochondrial membrane proteins to generate specific mitoROS in a mPTP formation and opening-independent manner. To further confirm this notion, we employed rotenone, a neurotoxin that has been demonstrated to inhibit mitochondrial complex I and is linked to mitoROS production, in MC65 cells to study the protective effects of 7 and Mito-TEMPO. As shown in FIG. 7D, rotenone significantly induced cell death of MC65 cells (75.6%) at 10 μM. Mito-TEMPO significantly protected MC65 cells from rotenone-induced cytotoxicity at 3 and 10 μM in a dose-dependent manner, while 7 did not show protection up to 1 μM, concentrations known to protect MC65 cells from −TC induced cytotoxicity. Taken together, these results suggest that upon production, AβOs enter or interact with the mitochondrial membrane to produce mitoROS that lead to the death of MC65 cells, and 7 blocks this interaction of AβOs with mitochondria, thus ultimately leading to its antioxidant and neuroprotective activities as demonstrated by the aforementioned assays. Given the fact that AβOs have been shown to induce tau hyperphosphorylation, neurofibrillary tangle formation, synaptic alteration, and neurodegeneration,[5, 37-40] the ability of 7 to block the interactions of AβOs with partner proteins indicates its use as an effective AD-modifying agent.

In addition to activity, it is essential to establish whether these compounds are able to cross the blood brain barrier (BBB) as they are destined to act within the central nervous system (CNS). Therefore, the potential brain penetration of 3, 5, and 7 was evaluated using the optimized parallel artificial membrane permeability-BBB (PAMPA-BBB) passive diffusion model, a well-established and widely used in vitro BBB model for molecules with limited water-solubility.[41, 42] The in vitro permeability ($P_e$) values of 3, 5, and 7 through a lipid extract of porcine brain were determined by using a mixture of PBS and ethanol in the ratio of 70:30. In the same assay, 10 commercial drugs with known CNS penetration were also tested as positive controls, and their experimental values were compared to reported values (Table 1).

TABLE 1

Permeability ($P_e$ $10^{-6}$ cm $s^{-1}$)$^a$ in the PAMPA-BBB Assay for Commercial Drugs (Used for Experimental Validation) and Compounds 3, 5, and 7 with their Predictive Penetration in the CNS.

| Commercial drugs | Bibl.[b] | $P_e$ (exp.) | Compd. | $P_e$ (exp.) | Prediction |
|---|---|---|---|---|---|
| Testosterone | 17.0 | 31.4 ± 2.4 | 7 | 7.9 ± 0.6 | CNS− |
| Verapamil | 16.0 | 31.2 ± 2.1 | 5 | 5.9 ± 0.4 | CNS− |
| Imipramine | 13.0 | 18.6 ± 1.8 | 3 | 6.5 ± 0.6 | CNS− |
| Desipramine | 12.0 | 28.5 ± 0.5 | | | |
| Promazine | 8.8 | 25.1 ± 1.4 | | | |

TABLE 1-continued

Permeability ($P_e \; 10^{-6}$ cm s$^{-1}$)$^a$ in the PAMPA-BBB Assay for Commercial Drugs (Used for Experimental Validation) and Compounds 3, 5, and 7 with their Predictive Penetration in the CNS.

| Commercial drugs | Bibl.$^b$ | $P_e$ (exp.) | Compd. | $P_e$ (exp.) | Prediction |
|---|---|---|---|---|---|
| Corticosterone | 5.1 | 10.9 ± 1.0 | | | |
| Piroxicam | 2.5 | 6.0 ± 0.3 | | | |
| Hydrocortisone | 1.9 | 10.0 ± 0.6 | | | |
| Caffeine | 1.3 | 8.2 ± 0.6 | | | |
| Ofloxacin | 0.8 | 5.3 ± 0.3 | | | |

$^a$PBS:EtOH (70:30). Data are the mean ± SD of 3 independent experiments.
$^b$Taken from Reference 41

The results gave a good linear correlation with $P_e$ (exp)=1.603 $P_e$ (bibl)+4.860 ($R^2$=0.876). From this equation and following the pattern established in the literature for BBB permeability prediction, we expect that compounds with $P_e$<8.1×10$^{-6}$ cm s$^{-1}$ will have low BBB permeability by passive diffusion. As shown in Table 1, all three compounds showed $P_e$ values under this limit with 7 giving the highest value, so we suspect that these analogs might experience some difficulty in reaching the brain by passive diffusion. However, considering the predictive nature of this assay and the existence of influx transporters in the BBB, for example caffeine is not able to cross BBB by passive diffusion, but it reaches brain through a nucleoside transport system, we could not rule out the possibility that our compounds can reach brain tissues by a carrier-mediated penetration mechanism. Therefore, we decided to test the BBB penetration in intact mice. Both compounds 5 and 7 exhibited comparable neuroprotection potencies in the MC65 cell model, and the preliminary mechanistic studies demonstrated that they share the same mode of actions. Therefore, based on the observed solubility and stability from our in vitro tests and also considering the cost of further in vivo studies using transgenic AD mice, we only selected 7 for further BBB penetration studies in mice.

Given the consideration that management of AD with medications would be a long term care process for patients and oral administration would significantly improve patient compliance, we tested 7 for its BBB permeability in male CD-1 mice (n=6) by oral administration at a dose of 50 mg/kg. To accurately quantify the amount of 7 that is delivered into brain tissue and rule out the possibility of biased interpretation from vascular trapping, we perfused the mice to wash out the vascular blood completely prior to collecting brain tissues. After oral administration, plasma samples were collected at 0.25, 0.5, 1, and 24 hours, and brain samples were collected at 1 and 24 hours. Collected samples were analyzed by LC-MS/MS and the results are shown in Table 2.

TABLE 2

Plasma and brain concentrations (nM) of 7 after oral administration at 50 mg/kg dose in CD-6 mice (n = 6).

| | 15 min | 30 min | 1 h | 24 h |
|---|---|---|---|---|
| Plasma | 773.80 ± 309.86 | 794.72 ± 301.34 | 883.12 ± 350.36 | 30.53 ± 11.96 |
| Brain | | | 555.40 ± 188.44 | 47.41 ± 11.19 |

Compound 7 exhibited a quick absorption profile as the plasma concentration reached 773±309.86 nM (n=6) 15 minutes after oral administration and was only slightly increased after 1 hour. The plasma and brain concentrations of 7 after 1 hour were 883.12±350.36 and 555.40±188.43 nM, respectively. This clearly indicates that 7 quickly and efficiently reached brain tissue after oral ingestion, thus confirming its BBB permeability. After 24 hours, the plasma and brain concentrations dropped to 30.53±11.96 and 47.41±11.19 nM, respectively. It is important to note that the brain concentration of 7 at this time point still remains above the neuroprotective EC$_{50}$ of 7 in MC65 cells (27.60±9.60 nM), suggesting that a once daily regimen should provide a sufficient amount of 7 in the brain tissue to be therapeutically effective.

In summary, hybrid compounds of curcumin (1) and melatonin (2) were designed and synthesized as neuroprotectants for AD. Initial biological characterization of 3 from in vitro assays established that the hybrid strategy is a viable approach in providing novel chemotypes with novel pharmacology. Further modifications identified 7 as a lead compound with potent neuroprotections in MC65 cells. Without being bound by theory, mechanistic studies suggested that antioxidative effects might be the major mechanism leading to their neuroprotection, and it is likely that the manifested antioxidative effects of 7 are through interference of the interactions of AβOs with the mitochondria in MC65 cells. Furthermore, 7 has been shown to penetrate the BBB efficiently after oral administration in intact mice, thus confirming that it is orally bioavailable and therapeutically relevant concentrations are attainable in CNS. These findings also support the hybridization strategy as a novel design approach to provide effective disease-modifying agents for AD.

ABBREVIATIONS

Aβ, amyloid-β; AβOs, amyloid-β oligomers; AD, Alzheimer's disease; AFM, atomic force microscopy; BBB, blood-brain barrier; CNS, central nervous system; DCFH-DA, dichlorofluorescein diacetate; DMPU, N,N'-dimethylpropyleneurea; DMEM, Dulbecco's modified eagle's medium; DMSO, dimethyl sulfoxide; ESI, electrospray ionization; FBS, fetal bovine serum; HPLC, high performance liquid chromatography; LC, liquid chromatography; mitoROS, mitochondrial reactive oxygen species; mPTP, mitochondrial permeability transition pore; MS, mass spectrometry; MTT, 3-(4,5-dimethylthiazol-2-yl)-2,5-diphenyltetrazolium bromide; NAC, N-acetylcysteine; PAMPA, parallel artificial membrane permeability; PBS, phosphate buffered saline; PMA, phosphomolybdic acid; ROS, reactive oxygen species; SAR, structure-activity relationship; SDS-PAGE, sodium dodecyl sulfate-polyacrylamide gel electrophoresis; SEM, standard error of mean; SRM, selected reaction monitoring; TBS, Tris buffered saline; TC, tetracycline; TFA, trifluoroacetic acid; THF, tetrahydrofuran; ThT, thioflavin T; TLC, thin-layer chromatography; TMS, tetramethylsilane.

Example 2

Figures 9A, 9B:
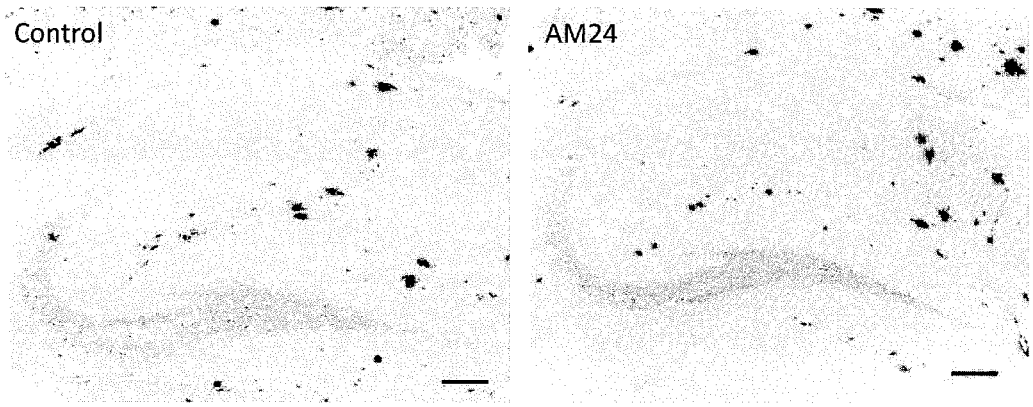
FIG. 9A-C. AM24 (7) (50 mg/kg) oral gavage treatment during 12 weeks in 4 month-old APP/PS1 transgenic animals. Immunochemistry was performed using anti-Aβ 1-16
Figure 9C:
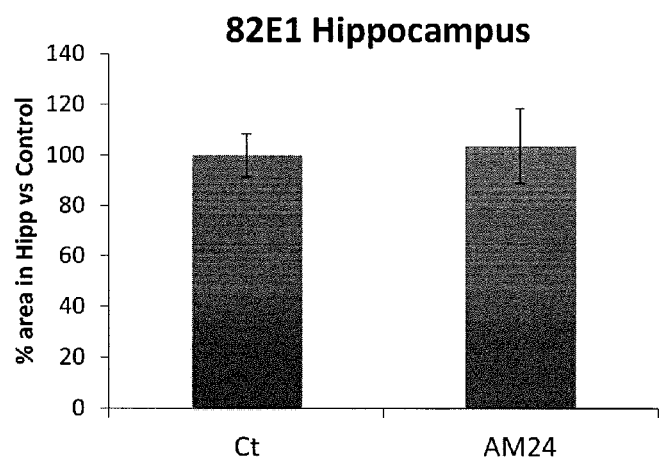
Figure 10A:
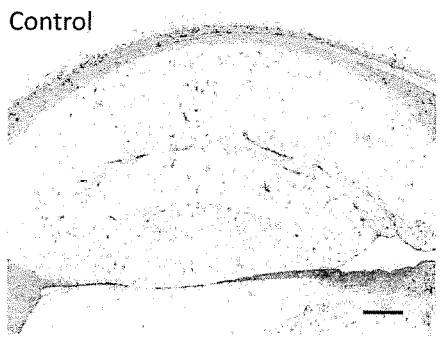
Figure 10B:
Figure 10C:
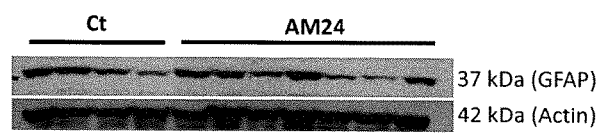
Figure 10D:
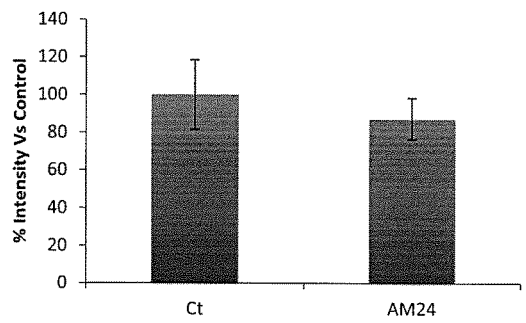
Figure 10E:
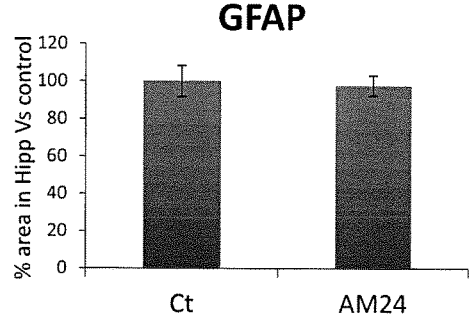

Effect of 5-(4-hydroxy-phenyl)-3-oxo-pentanoic acid [2-(5-methoxy-1H-indol-3-yl)-ethyl]-amide (AM24; compound 7) treatment in an AD mouse model APP/PS1 (amyloid precursor protein/presenilin-1) transgenic mice are a well known model for Alzheimer's disease. In this study, APP/PS1 mice were treated with 50 mg/kg of AM24 (compound 7) and the effects on cell type/morphology and the levels of several neuroinflammatory and stress markers was observed. After oral AM24 treatment over 12 weeks, there was a significant decrease in cortical and cortex/hippocampal amyloid plaques (FIG. 8A-D). However, there was no decrease in hippocampal plaques (FIG. 9A-C). Additionally, there was no change in the expression of glial fibrillary acid protein (GFAP), a neuroinflammation marker, in the hippocampus of AM24 treated animals (FIG. 10A-E). The total number (FIG. 11A-C) and type (FIG. 12A-C) of glial cells remained constant between the control and AM24 treated animals.

AM24 treatment promoted a significant decrease in expression of 8-Hydroxyguanosine (8OHG), a stress marker, in the hippocampus (FIG. 13A-C), however there was no change in expression of an oxidative stress marker, heme-oxygenase-1 (HO-1) (FIG. 14A-B). As shown in FIG. 15, a significant decrease in expression of the stress marker 4-hydroxy-2-nonenal (HNE) in AM24 treated animals was detected compared with saline animals (FIG. 15A-B). Finally, a powerful increase was observed in NADH Dehydrogenase-Complex I, induced by AM24 treatment (FIG. 16A-B).

Example 3

Synthesis of a Series of Analogs of Compound 3 and Evaluation of Neuroprotective Properties Materials and Methods Chemistry.

Reagents and solvents were obtained from commercial suppliers and used as received unless otherwise indicated. Reactions were monitored by thin-layer chromatography (TLC) (precoated silica gel 60F254 plates, EMD Chemicals) and visualized with UV light or by treatment with phosphomolybdic acid (PMA) or ninhydrin. Flash chromatography was performed on silica gel (200-300 mesh, Fisher Scientific) using solvents as indicated. $^1$HNMR and $^{13}$CNMR spectra were routinely recorded on a Bruker ARX 400 spectrometer. The NMR solvent used was CDCl$_3$ or CD$_3$OD as indicated. Tetramethylsilane (TMS) was used as the internal standard. The purity of target compounds was determined by HPLC using a Varian® 100-5 C18 250×4.6 mm column with UV detection (280 nm and 360 nm) (50% H$_2$O in acetonitrile and 0.1% TFA, and 30-50% H$_2$O in methanol and 0.1% TFA, two solvent systems) to be ≥95%. Synthesis of the designed analogs was achieved following the conditions in FIG. 17. Compounds 3-7, 9, and 10 were synthesized as described in Example 1. In FIGS. 18 and 19A-B, compound 4 is labeled 8a, 5 is labeled 8b, 6 is labeled 8c, and 7 is labeled 9.

Procedure A. Preparation of K30 (Compound 3).

Compound 10 (0.25 g, 0.47 mmol) was added to a solution of NaH (0.075 g, 1.87 mmol) in DMPU/THF (2 mL/2.2 mL) and cooled to 0° C. for 30 min. To this vanillin (0.085 g, 0.56 mmol) in THF (0.5 mL) was added dropwise. The solution was heated to 40° C. for 3 h. The solution was then cooled to room temperature and stirred overnight. The reaction was then quenched using NH$_4$Cl (0.5 mL). The solvent was removed under reduced pressure and the residual oil was purified by flash chromatography (Hexanes/Acetone: 50/50) to give 3 (0.06 g, 31%) as a light yellow solid. $^1$HNMR (400 MHz, CDCl$_3$) δ 8.03 (s, 1H), 7.56 (d, J=16.04 Hz, 1H), 7.23 (d, J=8.80 Hz, 1H), 7.09 (dd, J=8.28 Hz, 1.84 Hz, 1H), 7.04-6.99 (m, 3H), 6.93 (d, J=8.20 Hz, 1H), 6.85 (dd, J=8.80 Hz, 2.4 Hz, 1H), 6.59 (d, J=16.04 Hz, 1H), 3.92 (s, 3H), 3.86 (s, 3H), 3.63 (q, J=5.76 Hz, 2H), 3.58 (s, 2H), 2.96 (t, J=6.88 Hz, 2H); $^{13}$CNMR (100 MHz, CDCl$_3$) δ 195.31, 165.96, 154.09, 149.00, 147.00, 145.68, 131.56, 127.73, 126.48, 124.18, 123.30, 122.89, 115.00, 112.62, 112.43, 111.95, 109.83, 100.54, 56.03, 55.96, 47.30, 39.79, 25.24.

Preparation of ZSJ-II-136 (Compound 8d).

4-Methoxybenzaldehyde (0.076 g, 0.56 mmol) was reacted with 10 (0.25 g, 0.47 mmol) following Procedure A to give ZSJ-II-136 (0.07 g, 39%). $^1$H NMR (400 MHz, CDCl$_3$) δ 7.96 (br. s., 1H), 7.59 (d, J=16.06 Hz, 1H), 7.50 (d, J=8.80 Hz, 2H), 7.24 (d, J=9.03 Hz, 1H), 7.13 (br. s., 1H), 7.04 (s, 2H), 6.92 (d, J=8.80 Hz, 2H), 6.85 (dd, J=2.38, 8.91 Hz, 1H), 6.62 (d, J=16.06 Hz, 1H), 3.86 (s, 3H), 3.85 (s, 3H), 3.59-3.65 (m, 4H), 2.96 (t, J=6.90 Hz, 2H); $^{13}$C NMR (100 MHz, CDCl$_3$) δ 195.4, 165.8, 162.2, 154.1, 145.2, 131.5, 130.5, 127.7, 126.6, 123.4, 122.8, 114.6, 112.7, 112.5, 111.9, 100.5, 55.9, 55.4, 47.2, 39.7, 25.3.

Preparation of ZSJ-II-126 (Compound 8e).

1,3-Benzodioxole-5-carbaldehyde (0.070 g, 0.47 mmol) was reacted with 10 (0.25 g, 0.47 mmol) following Procedure A to give ZSJ-II-126 (0.05 g, 26%). $^1$H NMR (400 MHz, CDCl$_3$) δ 8.13 (br. s., 1H), 7.51 (d, J=16.06 Hz, 1H), 7.22 (d, J=8.78 Hz, 1H), 7.12 (br. s., 1H), 6.99-7.04 (m, 4H), 6.84 (dd, J=2.51, 8.78 Hz, 1H), 6.81 (d, J=8.53 Hz, 1H), 6.54 (d, J=15.81 Hz, 1H), 6.01 (s, 2H), 3.85 (s, 3H), 3.61 (q, J=6.78 Hz, 2H), 3.55 (s, 2H), 2.95 (t, J=6.80 Hz, 2H); $^{13}$C NMR (100 MHz, CDCl$_3$) δ 195.2, 165.8, 154.0, 150.4, 148.5, 145.1, 131.5, 127.7, 125.6, 123.7, 122.9, 112.6, 112.4, 111.9, 108.7, 106.7, 101.7, 100.5, 55.9, 47.3, 39.7, 25.2.

Preparation of ZSJ-II-131 (Compound 8f).

3,4-Dimethoxybenzaldehyde (0.093 g, 0.56 mmol) was reacted with 10 (0.25 g, 0.47 mmol) following Procedure A to give ZSJ-II-131 (0.075 g, 38%). $^1$H NMR (400 MHz, CDCl$_3$) δ 8.15 (br. s., 1H), 7.58 (d, J=13.55 Hz, 1H), 7.22 (d, J=8.78 Hz, 1H), 7.14 (d, J=8.28 Hz, 1H), 7.01-7.09 (m, 4H), 6.88 (d, J=8.53 Hz, 1H), 6.84 (dd, J=1.51, 8.78 Hz, 1H), 6.62 (d, J=16.06 Hz, 1H), 3.92 (s, 3H), 3.91 (s, 3H), 3.86 (s, 3H), 3.58-3.65 (m, 4H), 2.96 (t, J=6.90 Hz, 2H); $^{13}$C NMR (100 MHz, CDCl$_3$) δ 195.3, 165.8, 154.0, 152.0, 149.3, 145.4, 131.5, 127.7, 126.9, 123.7, 123.6, 122.9, 112.5, 112.3, 111.9, 111.1, 110.0, 100.5, 55.9, 47.3, 39.7, 25.2.

Preparation of AM44 (Compound 8g).

3,4-Dihydroxybenzaldehyde (0.077 g, 0.56 mmol) was reacted with 10 (0.25 g, 0.47 mmol) following Procedure B to give AM44 (0.035 g, 19%). $^1$H NMR (400 MHz, CDCl$_3$) δ 7.53 (d, J=16.06 Hz, 1H), 7.20 (d, J=8.78 Hz, 1H), 7.07-7.10 (m, 1H), 7.03-7.07 (m, 2H), 6.96 (d, J=7.53 Hz, 1H), 6.78 (d, J=8.03 Hz, 1H), 6.74 (dd, J=2.26, 8.78 Hz, 1H), 6.60 (d, J=15.81 Hz, 1H), 3.78-3.83 (m, 3H), 3.49-3.55 (m, 2H), 3.31 (s, 2H), 2.93 (t, J=7.03 Hz, 2H); $^{13}$C NMR (100 MHz, CD$_3$OD) δ 196.3, 169.7, 155.1, 150.7, 147.2, 147.1, 133.6, 129.2, 127.6, 124.5, 124.0, 123.5, 116.8, 115.6, 113.0, 112.7, 101.6, 56.6, 41.6, 31.0, 26.3.

Preparation of AM43 (Compound 8h).

4-Hydroxy-3,5-dimethoxybenzaldehyde (0.129 g, 0.71 mmol) was reacted with 10 (0.25 g, 0.47 mmol) following Procedure B to give AM43 (0.068 g, 33%). $^1$H NMR (400 MHz, CDCl$_3$) δ 8.20 (br. s., 1H), 7.54 (d, J=16.06 Hz, 1H), 7.23 (d, J=8.53 Hz, 1H), 7.11 (t, J=5.40 Hz, 1H), 7.03 (dd, J=2.26, 6.53 Hz, 2H), 6.84 (dd, J=2.51, 8.78 Hz, 1H), 6.78 (s, 2H), 6.61 (d, J=16.06 Hz, 1H), 3.90 (s, 6H), 3.85 (s, 3H), 3.73 (s, 1H), 3.58-3.65 (m, 4H), 2.96 (t, J=7.00 Hz, 2H); $^{13}$C NMR (100 MHz, CDCl$_3$) δ 195.1, 165.9, 154.0, 147.3, 145.9, 138.1, 131.5, 127.7, 125.3, 123.5, 122.9, 112.4, 112.3, 111.9, 105.8, 100.5, 56.4, 55.9, 47.4, 43.4, 39.8, 25.2.

Preparation of AM14 (Compound 8i).

4-(Dimethylamino)benzaldehyde (0.084 g, 0.56 mmol) was reacted with 10 (0.25 g, 0.47 mmol) following Procedure A to give AM14 (0.047 g, 25%). $^1$H NMR (400 MHz, CDCl$_3$) δ 8.15 (br. s., 1H), 7.59 (d, J=15.81 Hz, 1H), 7.44 (d, J=9.03 Hz, 2H), 7.32 (t, J=5.77 Hz, 1H), 7.24 (d, J=8.78 Hz, 1H), 7.05 (dd, J=2.26, 9.54 Hz, 2H), 6.86 (dd, J=2.51, 8.78 Hz, 1H), 6.63-6.69 (m, 2H), 6.55 (d, J=15.81 Hz, 1H), 3.87 (s, 3H), 3.63 (q, J=6.78 Hz, 2H), 3.58 (s, 2H), 3.04 (s, 6H), 2.97 (t, J=6.90 Hz, 2H); $^{13}$C NMR (100 MHz, CDCl$_3$) δ 195.2, 166.3, 154.0, 152.4, 146.2, 131.5, 130.7, 127.7, 122.9, 121.5, 120.4, 112.6, 112.3, 111.9, 111.8, 100.5, 55.9, 46.9, 40.0, 39.7, 25.2.

Preparation of ZSJ-II-128 (Compound 8j).

Nicotinaldehyde (0.055 g, 0.51 mmol) was reacted with 10 (0.25 g, 0.47 mmol) following Procedure A to give ZSJ-II-128 (0.055 g, 32%). $^1$H NMR (400 MHz, CDCl$_3$) δ 13.59 (s, 1H), 8.65 (s, 1H), 8.55 (d, J=4.52 Hz, 1H), 8.13 (br. s., 1H), 7.76 (d, J=8.03 Hz, 1H), 7.50 (d, J=16.06 Hz, 1H), 7.23-7.27 (m, 1H), 7.15 (d, J=8.80 Hz, 1H), 6.94 (s, 1H), 6.86 (br. s., 1H), 6.77 (dd, J=2.50, 8.80 Hz, 1H), 6.71 (d, J=16.31 Hz, 1H), 3.78 (s, 3H), 3.50-3.57 (m, 4H), 2.89 (t, J=6.90 Hz, 2H); $^{13}$C NMR (100 MHz, CDCl$_3$) δ 194.8, 154.1, 151.6, 150.3, 143.8, 141.3, 134.6, 133.7, 131.5, 127.3, 122.8, 112.6, 112.5, 111.9, 100.5, 94.4, 55.9, 39.8, 25.2.

Preparation of AM6 (Compound 8k).

Isonicotinaldehyde (0.060 g, 0.56 mmol) was reacted with 10 (0.25 g, 0.47 mmol) following Procedure A to give AM6 (0.065 g, 38%). $^1$H NMR (400 MHz, CDCl$_3$) δ 13.64 (br. s., 1H), 8.63 (d, J=6.02 Hz, 1H), 8.54 (d, J=5.77 Hz, 1H), 8.46 (br. s., 1H), 7.46 (d, J=16.06 Hz, 1H), 7.32 (d, J=6.02 Hz, 1H), 7.23 (s, 1H), 6.99 (d, J=2.00 Hz, 1H), 6.92 (br. s., 1H), 6.86 (dd, J=2.26, 8.53 Hz, 1H), 6.46 (d, J=15.81 Hz, 1H), 3.83 (s, 3H), 3.55-3.65 (m, 4H), 2.97 (t, J=7.00 Hz, 2H); $^{13}$C NMR (100 MHz, CDCl$_3$) δ 194.8, 171.4, 165.9, 154.3, 150.4, 142.0, 132.4, 129.3, 127.0, 122.1, 121.4, 112.7, 112.5, 112.0, 100.5, 95.3, 56.0, 48.1, 39.5, 25.2.

Preparation of AM4 (Compound 8l).

2-Furaldehyde (0.054 g, 0.56 mmol) was reacted with 10 (0.25 g, 0.47 mmol) following Procedure A to give AM4 (0.025 g, 15%). $^1$H NMR (400 MHz, CDCl$_3$) δ 8.01 (br. s., 1H), 7.52 (d, J=1.51 Hz, 1H), 7.37 (d, J=15.81 Hz, 1H), 7.21-7.25 (m, 1H), 7.12 (br. s, 1H), 7.04 (d, J=2.51 Hz, 2H), 6.85 (dd, J=2.38, 8.66 Hz, 1H), 6.72 (d, J=3.51 Hz, 1H), 6.62 (d, J=15.81 Hz, 1H), 6.50 (dd, J=1.88, 3.39 Hz, 1H), 3.86 (s, 1H), 3.58-3.65 (m, 2H), 3.55 (s, 2H), 2.96 (t, J=7.03 Hz, 2H); $^{13}$C NMR (100 MHz, CDCl$_3$) Shift 195.0, 165.8, 154.1, 150.7, 145.7, 131.5, 130.9, 127.7, 122.9, 122.8, 117.2, 112.8, 112.7, 112.4, 111.9, 100.6, 55.9, 47.6, 39.7, 25.2.

Preparation of AM5 (Compound 8m).

3-Furaldehyde (0.054 g, 0.56 mmol) was reacted with 10 (0.25 g, 0.47 mmol) following Procedure A to give AM5 (0.020 g, 12%). $^1$H NMR (400 MHz, CDCl$_3$) δ 7.99 (br. s., 1H), 7.73 (s, 1H), 7.55 (d, J=15.81 Hz, 1H), 7.46 (t, J=1.38 Hz, 1H), 7.26 (d, J=8.78 Hz, 1H), 7.12 (br. s., 1H), 7.05 (d, J=2.26 Hz, 2H), 6.87 (dd, J=2.26, 8.78 Hz, 1H), 6.61 (d, J=1.76 Hz, 1H), 6.47 (d, J=16.06 Hz, 1H), 3.87 (s, 3H), 3.60-3.66 (m, 2H), 3.57 (s, 2H), 2.97 (t, J=6.90 Hz, 2H); $^{13}$C NMR (100 MHz, CDCl$_3$) δ 165.8, 154.1, 146.0, 144.8, 135.4, 131.5, 125.6, 122.8, 122.6, 112.6, 112.5, 111.9, 107.3, 100.5, 55.9, 47.1, 39.8, 25.2.

Results

Design and Synthesis of Analogs of 3.

Given the promising results of 3 as a potential neuroprotectant, a series of congeners of 3 (FIG. 2B and FIG. 18) were synthesized to conduct SAR studies of this chemotype. As shown in FIG. 18, the modifications are mainly focused on the phenyl ring of 3 and the double bond between the β-ketone and the phenyl ring, and fourteen analogs in total were designed. Compounds 4-7, AM3, AM4, AM5, AM6, AM12, AM14, AM42, AM43, AM44, ZSJ-II-126, ZSJ-II-128, ZSJ-II-131, ZSJ-II-132, and ZSJ-II-136 were designed to evaluate the importance of the 4-OH and 3-CH$_3$O substitutions, the position preference of these substituents, using a bioisosteric replacement strategy to assess whether such replacements would improve biological activity, as well as to investigate potential H-bond interactions and the preference of position of the heteroatoms on these rings and the nature of electron-donating effects on the neuroprotective activity of 3. Lastly, analog 9 was designed to shed light on the importance of the double bond and the related conjugation effects of the structure on biological activity.

Evaluation of Analogs of 3 in MC65 Cells.

All compounds were first tested for their protection of MC65 cells from −TC induced toxicity at a concentration of 0.3 μM, and the results are shown in FIG. 19A. Removal of 4-OH from 3 as demonstrated by compound 4 (8a) led to a complete loss of neuroprotection in MC65 cells (FIG. 19A). However, removal of 3-CH$_3$O from 3 did not affect its biological activity as compound 5 (8b) showed significant neuroprotection in MC65 cells at the tested concentration (FIG. 19A). These results clearly indicate that the 4-OH group is essential to the neuroprotective activities of 3. This notion is further supported by the results of the unsubstituted analog 6 (8C), the 4-CH$_3$O analog ZSJ-II-136 (8d), the 3,4-methylenedioxy analog ZSJ-II-126 (8e), and the 3,4-dimethoxy analog ZSJ-II-131 (8f), all of which exhibited diminished protection of MC65 cells (FIG. 19A). The results of these analogs may also indicate that H-bond interactions with the 4-OH group play an important role in the biological activity of 3. Interestingly, adding an OH— group at the 3-position of 5 (8b), as demonstrated by compound AM44 (8g), reduced neuroprotection by 29.19% compared to 5 (FIG. 19A), while adding a CH$_3$O— group at the 5-position of 3 (AM43; 8h) led to a significant loss of neuroprotection (~61.53% loss) compared to 3 (FIG. 19A and FIG. 4A). This might suggest that the specific interaction site with the 4-OH moiety cannot tolerate steric hindrance. This notion is further reflected by compound AM14 (8i) with a (CH$_3$)$_2$N— substitution at the para-position of the phenyl ring as it showed only weak neuroprotection in MC65 cells (~0.20% protection compared to −TC control) (FIG. 19A). Replacement of the 4-OH-phenyl ring of 3 with a pyridine moiety resulted in two compounds, with the 3-substituted pyridine analog ZSJ-II-128 (8j) being inactive, while the 4-substituted pyridine analog AM6 (8k) was moderately active in protecting MC65 cells (~33% protection compared to −TC control) (FIG. 19A). The activity of AM6 (8k) might somehow echo the neuroprotective activity of 5 since the N of the pyridine moiety is positioned as the 4-OH in compound 5. Interestingly, for the furan substituted analogs AM4 (8l) and AM5 (8m), the 2-furan substituted analog AM4 (8l) did not show neuroprotection, while the 3-furan substituted analog AM5 (8m) exhibited moderate protection (~48% protection compared to −TC control) to MC65 cells (FIG. 19A), which is consistent with the results of ZSJ-II-128 (8j) and AM6 (8k) considering the positions of the O in the furan ring.

To further evaluate the role of the double bond between the phenyl ring and the β-ketone, compound 9 was synthesized and evaluated at a concentration of 0.3 µM. Notably, 9 exhibited significant and comparable protection of MC65 cells with 5 (8b), thus suggesting that the double bond and the conjugation system with the phenyl ring is not necessary to produce neuroprotection in MC65 cells for these analogs (FIG. 19B). This further suggests that the electronic effects of the substitutions on the phenyl ring may not play an essential role in the biological activity of this chemotype, which is consistent with the results discussed above.

REFERENCES

1. Alzheimer's Association. (2013) 2013 Alzheimer's Disease Facts and Figures, *Alzheimers Dement.* 9, 208-245.
2. Hardy, J., and Selkoe, D. J. (2002) The amyloid hypothesis of Alzheimer's disease: progress and problems on the road to therapeutics, *Science (New York, N.Y.)* 297, 353-356.
3. Kirkitadze, M. D., Bitan, G., and Teplow, D. B. (2002) Paradigm shifts in Alzheimer's disease and other neurodegenerative disorders: the emerging role of oligomeric assemblies, *J. Neurosci. Res.* 69, 567-577.
4. Walsh, D. M., and Selkoe, D. J. (2007) A beta oligomers—a decade of discovery, *J. Neurochem.* 101, 1172-1184.
5. Selkoe, D. J. (2008) Soluble oligomers of the amyloid beta-protein impair synaptic plasticity and behavior, *Behav. Brain Res.* 192, 106-113.
6. Bush, A. I. (2008) Drug development based on the metals hypothesis of Alzheimer's disease, *J. Alzheimers Dis.* 15, 223-240.
7. Zhu, X., Su, B., Wang, X., Smith, M. A., and Perry, G. (2007) Causes of oxidative stress in Alzheimer disease, *Cell. Mol. Life Sci.* 64, 2202-2210.
8. Viegas-Junior, C., Danuello, A., da Silva Bolzani, V., Barreiro, E. J., and Fraga, C. A. (2007) Molecular hybridization: a useful tool in the design of new drug prototypes, *Curr. Med. Chem.* 14, 1829-1852.
9. Tietze, L. F., Bell, H. P., and Chandrasekhar, S. (2003) Natural product hybrids as new leads for drug discovery, *Angew. Chem., Int. Ed.* 42, 3996-4028.
10. Yang, F., Lim, G. P., Begum, A. N., Ubeda, O. J., Simmons, M. R., Ambegaokar, S. S., Chen, P. P., Kayed, R., Glabe, C. G., Frautschy, S. A., and Cole, G. M. (2005) Curcumin inhibits formation of amyloid beta oligomers and fibrils, binds plaques, and reduces amyloid in vivo, *J. Biol. Chem.* 280, 5892-5901.
11. Kim, J., Lee, H. J., and Lee, K. W. (2010) Naturally occurring phytochemicals for the prevention of Alzheimer's disease, *J. Neurochem.* 112, 1415-1430.
12. X., W. (2009) The antiapoptotic activity of melatonin in neurodegenerative diseases., *CNS Neurosci. Ther.* 15, 345-357.
13. Rosales-Corral, S. A., Acuna-Castroviejo, D., Coto-Montes, A., Boga, J. A., Manchester, L. C., Fuentes-Broto, L., Korkmaz, A., Ma, S., Tan, D. X., and Reiter, R. J. (2012) Alzheimer's disease: pathological mechanisms and the beneficial role of melatonin, *J. Pineal Res.* 52, 167-202.
14. Frautschy, S. A., and Cole, G. M. (2010) Why pleiotropic interventions are needed for Alzheimer's disease, *Mol. Neurobiol.* 41, 392-409.
15. Pevet, P. (2000) Melatonin and biological rhythms, *Biol. Signals Recept.* 9, 203-212.
16. Carpentieri, A., Diaz de Barboza, G., Areco, V., Peralta Lopez, M., and Tolosa de Talamoni, N. (2012) New perspectives in melatonin uses, *Pharmacol. Res.* 65, 437-444.
17. Zhou, J. N., Liu, R. Y., Kamphorst, W., Hofman, M. A., and Swaab, D. F. (2003) Early neuropathological Alzheimer's changes in aged individuals are accompanied by decreased cerebrospinal fluid melatonin levels, *J. Pineal Res.* 35, 125-130.
18. Hatfield, C. F., Herbert, J., van Someren, E. J., Hodges, J. R., and Hastings, M. H. (2004) Disrupted daily activity/rest cycles in relation to daily cortisol rhythms of home-dwelling patients with early Alzheimer's dementia, *Brain: a journal of neurology* 127, 1061-1074.
19. Rosales-Corral, S., Acuna-Castroviejo, D., Tan, D. X., Lopez-Armas, G., Cruz-Ramos, J., Munoz, R., Melnikov, V. G., Manchester, L. C., and Reiter, R. J. (2012) Accumulation of exogenous amyloid-beta peptide in hippocampal mitochondria causes their dysfunction: a protective role for melatonin, *Oxid. Med. Cell. Longev.* 2012, 843649.
20. Pandi-Perumal, S. R., BaHammam, A. S., Brown, G. M., Spence, D. W., Bharti, V. K., Kaur, C., Hardeland, R., and Cardinali, D. P. (2013) Melatonin antioxidative defense: therapeutical implications for aging and neurodegenerative processes, *Neurotox. Res.* 23, 267-300.
21. Hardeland, R. (2012) Melatonin in aging and disease—multiple consequences of reduced secretion, options and limits of treatment, *Aging Dis.* 3, 194-225.
1. Alzheimer's Association. (2013) 2013 Alzheimer's Disease Facts and Figures, *Alzheimers Dement.* 9, 208-245.
2. Hardy, J., and Selkoe, D. J. (2002) The amyloid hypothesis of Alzheimer's disease: progress and problems on the road to therapeutics, *Science (New York, N.Y.)* 297, 353-356.
3. Kirkitadze, M. D., Bitan, G., and Teplow, D. B. (2002) Paradigm shifts in Alzheimer's disease and other neurodegenerative disorders: the emerging role of oligomeric assemblies, *J. Neurosci. Res.* 69, 567-577.
4. Walsh, D. M., and Selkoe, D. J. (2007) A beta oligomers—a decade of discovery, *J. Neurochem.* 101, 1172-1184.
5. Selkoe, D. J. (2008) Soluble oligomers of the amyloid beta-protein impair synaptic plasticity and behavior, *Behav. Brain Res.* 192, 106-113.
6. Bush, A. I. (2008) Drug development based on the metals hypothesis of Alzheimer's disease, *J. Alzheimers Dis.* 15, 223-240.
7. Zhu, X., Su, B., Wang, X., Smith, M. A., and Perry, G. (2007) Causes of oxidative stress in Alzheimer disease, *Cell. Mol. Life Sci.* 64, 2202-2210.
8. Viegas-Junior, C., Danuello, A., da Silva Bolzani, V., Barreiro, E. J., and Fraga, C. A. (2007) Molecular hybridization: a useful tool in the design of new drug prototypes, *Curr. Med. Chem.* 14, 1829-1852.
9. Tietze, L. F., Bell, H. P., and Chandrasekhar, S. (2003) Natural product hybrids as new leads for drug discovery, *Angew. Chem., Int. Ed.* 42, 3996-4028.
10. Yang, F., Lim, G. P., Begum, A. N., Ubeda, O. J., Simmons, M. R., Ambegaokar, S. S., Chen, P. P., Kayed, R., Glabe, C. G., Frautschy, S. A., and Cole, G. M. (2005) Curcumin inhibits formation of amyloid beta oligomers and fibrils, binds plaques, and reduces amyloid in vivo, *J. Biol. Chem.* 280, 5892-5901.
11. Kim, J., Lee, H. J., and Lee, K. W. (2010) Naturally occurring phytochemicals for the prevention of Alzheimer's disease, *J. Neurochem.* 112, 1415-1430.
12. X., W. (2009) The antiapoptotic activity of melatonin in neurodegenerative diseases., *CNS Neurosci. Ther.* 15, 345-357.
13. Rosales-Corral, S. A., Acuna-Castroviejo, D., Coto-Montes, A., Boga, J. A., Manchester, L. C., Fuentes-Broto, L., Korkmaz, A., Ma, S., Tan, D. X., and Reiter, R. J. (2012) Alzheimer's disease: pathological mechanisms and the beneficial role of melatonin, *J. Pineal Res.* 52, 167-202.
14. Frautschy, S. A., and Cole, G. M. (2010) Why pleiotropic interventions are needed for Alzheimer's disease, *Mol. Neurobiol.* 41, 392-409.
15. Pevet, P. (2000) Melatonin and biological rhythms, *Biol. Signals Recept.* 9, 203-212.
16. Carpentieri, A., Diaz de Barboza, G., Areco, V., Peralta Lopez, M., and Tolosa de Talamoni, N. (2012) New perspectives in melatonin uses, *Pharmacol. Res.* 65, 437-444.
17. Zhou, J. N., Liu, R. Y., Kamphorst, W., Hofman, M. A., and Swaab, D. F. (2003) Early neuropathological Alzheimer's changes in aged individuals are accompanied by decreased cerebrospinal fluid melatonin levels, *J. Pineal Res.* 35, 125-130.
18. Hatfield, C. F., Herbert, J., van Someren, E. J., Hodges, J. R., and Hastings, M. H. (2004) Disrupted daily activity/rest cycles in relation to daily cortisol rhythms of home-dwelling patients with early Alzheimer's dementia, *Brain: a journal of neurology* 127, 1061-1074.
19. Rosales-Corral, S., Acuna-Castroviejo, D., Tan, D. X., Lopez-Armas, G., Cruz-Ramos, J., Munoz, R., Melnikov, V. G., Manchester, L. C., and Reiter, R. J. (2012) Accumulation of exogenous amyloid-beta peptide in hippocampal mitochondria causes their dysfunction: a protective role for melatonin, *Oxid. Med. Cell. Longev.* 2012, 843649.
20. Pandi-Perumal, S. R., BaHammam, A. S., Brown, G. M., Spence, D. W., Bharti, V. K., Kaur, C., Hardeland, R., and Cardinali, D. P. (2013) Melatonin antioxidative defense: therapeutical implications for aging and neurodegenerative processes, *Neurotox. Res.* 23, 267-300.
21. Hardeland, R. (2012) Melatonin in aging and disease—multiple consequences of reduced secretion, options and limits of treatment, *Aging Dis.* 3, 194-225.
22. Esatbeyoglu, T., Huebbe, P., Ernst, I. M., Chin, D., Wagner, A. E., and Rimbach, G. (2012) Curcumin—from molecule to biological function, *Angew. Chem., Int. Ed.* 51, 5308-5332.
23. Wong, Y.-S., Peuchmaur, M. A., Marechal, E., Botte, C., Vial, H. J., and Saidani, N. (2009) Preparation of novel polyspirane compounds for treating malaria or toxoplasmosis, p 122 pp., Universite Joseph Fourier, Fr.
24. Sopher, B. L., Fukuchi, K., Kavanagh, T. J., Furlong, C. E., and Martin, G. M. (1996) Neurodegenerative mechanisms in Alzheimer disease. A role for oxidative damage in amyloid beta protein precursor-mediated cell death, *Mol. Chem. Neuropathol.* 29, 153-168.
25. Lenhart, J. A., Ling, X., Gandhi, R., Guo, T. L., Gerk, P. M., Brunzell, D. H., and Zhang, S. (2010) "Clicked" bivalent ligands containing curcumin and cholesterol as multifunctional abeta oligomerization inhibitors: design, synthesis, and biological characterization, *J. Med. Chem.* 53, 6198-6209.
26. Liu, K., Gandhi, R., Chen, J., and Zhang, S. (2012) Bivalent ligands targeting multiple pathological factors involved in Alzheimer's disease, *ACS Med. Chem. Lett.* 3, 942-946.
27. McClain, D. E., Kalinich, J. F., and Ramakrishnan, N. (1995) Trolox inhibits apoptosis in irradiated MOLT-4 lymphocytes, *Faseb J.* 9, 1345-1354.
28. Aruoma, O. I., Halliwell, B., Hoey, B. M., and Butler, J. (1989) The antioxidant action of N-acetylcysteine: its reaction with hydrogen peroxide, hydroxyl radical, superoxide, and hypochlorous acid, *Free Radic. Biol. Med.* 6, 593-597.
29. Atkuri, K. R., Mantovani, J. J., Herzenberg, L. A., and Herzenberg, L. A. (2007) N-Acetylcysteine—a safe antidote for cysteine/glutathione deficiency, *Curr. Opin. Pharmacol.* 7, 355-359.
30. Lezoualc'h, F., Skutella, T., Widmann, M., and Behl, C. (1996) Melatonin prevents oxidative stress-induced cell death in hippocampal cells, *Neuroreport* 7, 2071-2077.
31. Ishimura, A., Ishige, K., Taira, T., Shimba, S., Ono, S., Ariga, H., Tezuka, M., and Ito, Y. (2008) Comparative study of hydrogen peroxide- and 4-hydroxy-2-nonenal-induced cell death in HT22 cells, *Neurochem. Int.* 52, 776-785.
32. Reale, M., Pesce, M., Priyadarshini, M., Kamal, M. A., and Patruno, A. (2012) Mitochondria as an easy target to oxidative stress events in Parkinson's disease, *CNS Neurol. Disord. Drug Targets* 11, 430-438.
33. Hirst, J., King, M. S., and Pryde, K. R. (2008) The production of reactive oxygen species by complex I, *Biochem. Soc. Trans.* 36, 976-980.
34. Martin, L. J. (2010) Olesoxime, a cholesterol-like neuroprotectant for the potential treatment of amyotrophic lateral sclerosis, *IDrugs: the investigational drugs journal* 13, 568-580.
35. Nazarewicz, R. R., Dikalova, A., Bikineyeva, A., Ivanov, S., Kirilyuk, I. A., Grigor'ev, I. A., and Dikalov, S. I. (2013) Does scavenging of mitochondrial superoxide attenuate cancer prosurvival signaling pathways?, *Antioxid. Redox. Signal* 19, 344-349.
36. Brookes, P. S., Yoon, Y., Robotham, J. L., Anders, M. W., and Sheu, S. S. (2004) Calcium, ATP, and ROS: a mitochondrial love-hate triangle, *Am. J. Physiol. Cell. Physiol.* 287, C817-833.
37. Umeda, T., Maekawa, S., Kimura, T., Takashima, A., Tomiyama, T., and Mori, H. (2014) Neurofibrillary tangle formation by introducing wild-type human tau into APP transgenic mice, *Acta Neuropathol.*
38. De Felice, F. G., Wu, D., Lambert, M. P., Fernandez, S. J., Velasco, P. T., Lacor, P. N., Bigio, E. H., Jerecic, J., Acton, P. J., Shughrue, P. J., Chen-Dodson, E., Kinney, G. G., and Klein, W. L. (2008) Alzheimer's disease-type neuronal tau hyperphosphorylation induced by A beta oligomers, *Neurobiol. Aging* 29, 1334-1347.
39. Jin, M., Shepardson, N., Yang, T., Chen, G., Walsh, D., and Selkoe, D. J. (2011) Soluble amyloid beta-protein dimers isolated from Alzheimer cortex directly induce Tau hyperphosphorylation and neuritic degeneration, *Proc. Natl. Acad. Sci. U.S.A.* 108, 5819-5824.
40. Klein, W. L. (2013) Synaptotoxic amyloid-beta oligomers: a molecular basis for the cause, diagnosis, and treatment of Alzheimer's disease?, *J. Alzheimers Dis.* 33 *Suppl* 1, S49-65.
41. Di, L., Kerns, E. H., Fan, K., McConnell, O. J., and Carter, G. T. (2003) High throughput artificial membrane permeability assay for blood-brain barrier, *Eur. J. Med. Chem.* 38, 223-232.

42. Fernandez-Bachiller, M. I., Perez, C., Monjas, L., Rademann, J., and Rodriguez-Franco, M. I. (2012) New tacrine-4-oxo-4H-chromene hybrids as multifunctional agents for the treatment of Alzheimer's disease, with cholinergic, antioxidant, and beta-amyloid-reducing properties, *J. Med. Chem.* 55, 1303-1317.

43. Stine, W. B., Jr., Dahlgren, K. N., Krafft, G. A., and LaDu, M. J. (2003) In vitro characterization of conditions for amyloid-beta peptide oligomerization and fibrillogenesis, *J. Biol. Chem.* 278, 11612-11622.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A compound having the general formula:

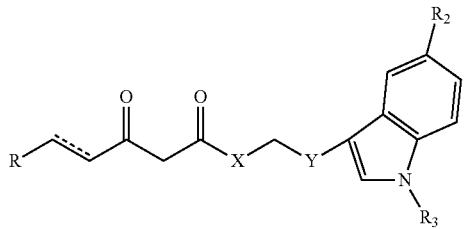

wherein
R is a substituted aromatic group, or an unsubstituted aromatic group, or a substituted heteroaromatic group or an unsubstituted heteroaromatic group;
R2 is selected from the group consisting of H, OH, NH$_2$, NO$_2$ and C$_1$-C$_8$ alkoxyl;
R3 is selected from the group consisting of H and C$_1$-C$_4$ alkyl;
X is S or O or NH or substituted-N, wherein the substituent is selected from the group consisting of C$_1$-C$_8$ alkyl, isopropyl, tert-butyl, and an saturated or unsaturated monocyclic ring with ring size ranging from 3-7 which is optionally substituted with one or more substituents selected from the group consisting of C$_1$-C$_8$ alkyl, C$_1$-C$_8$ alkoxyl, C$_1$-C$_8$ alkylcarbonyl, halogen, hydroxyl, amino, nitro, and cyano; and
Y is selected from the group consisting of C$_1$-C$_4$ alkyl with the proviso that if there is a double bond adjacent to the R group, then R is not a phenyl ring substituted by OCH3.

2. The compound of claim 1, wherein said aromatic or heteroaromatic group is substituted with a hydroxyl or a substituted or unsubstituted amino group.

3. The compound of claim 1, wherein said substituted or unsubstituted aromatic or heteroaromatic group is a substituted or unsubstituted heteroaromatic group which includes an oxygen or a nitrogen as the heteroatom.

4. The compound of claim 2, wherein the aromatic or heteroaromatic group is further substituted with a substituent selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano.

5. The compound of claim 3, wherein the aromatic or heteroaromatic group is further substituted with a substituent selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano.

6. The compound of claim 1, having the general formula of formula I:

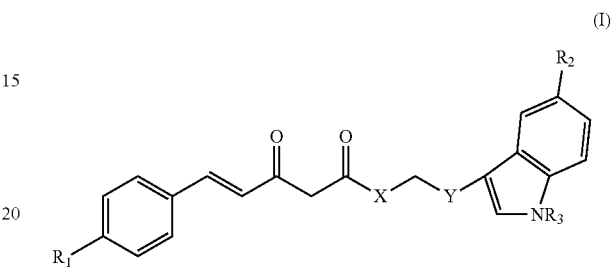

wherein R1 is selected from the group consisting of: H, OH and NH$_2$ and substituted-N wherein the substituent is selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano.

7. The compound of claim 1, having the general formula of formula II:

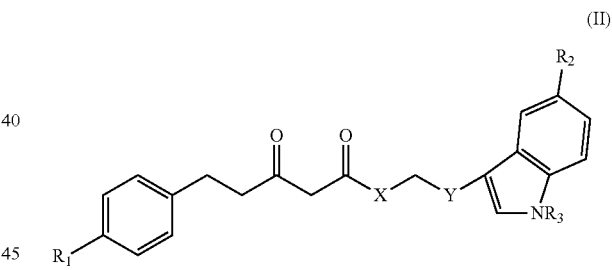

wherein R1 is selected from the group consisting of: H, OH and NH$_2$ and substituted-N wherein the substituent is selected from the group consisting of C$_1$-C$_8$ alkyl, wherein the phenyl is optionally substituted with one or more substituents at positions 2, 3, 5, and 6 selected from the group consisting of C$_1$-C$_8$ alkyl, C$_1$-C$_8$ alkoxyl, C$_1$-C$_8$ alkylcarbonyl, halogen, hydroxyl, amino, nitro, and cyano.

8. The compound of claim 1, wherein said compound is 5-(4-Hydroxy-3-methoxy-phenyl)-3-oxo-pent-4-enoic acid [2-(5-methoxy-1H-indol-3-yl)-ethyl]-amide.

9. The compound of claim 1, wherein said compound is 5-(4-hydroxy-phenyl)-3-oxo-pentanoic acid [2-5-methoxy-1H-indole-3-yl)-ethyl]-amide.

10. The compound of claim 1, wherein said compound is 5-(4-hydroxy-phenyl)-3-oxo-pentanoic acid [2-5-methoxy-1H-indole-3-yl)-ethyl]-amide.

11. A composition, comprising:
a compound having the general formula:

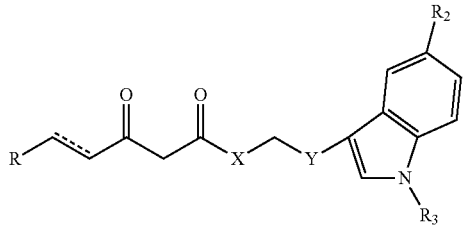

wherein
  R is a substituted or unsubstituted aromatic or heteroaromatic group;
  R2 is selected from the group consisting of H, OH, $NH_2$, $NO_2$ and $C_1$-$C_8$ alkoxyl;
  R3 is selected from the group consisting of H and $C_1$-$C_4$ alkyl;
  X is S or O or NH or substituted-N, wherein the substituent is selected from the group consisting of $C_1$-$C_8$ alkyl, isopropyl, tert-butyl, and a saturated or unsaturated monocyclic ring with ring size ranging from 3-7, which is optionally substituted with one or more substituents selected from the group consisting of $C_1$-$C_8$ alkyl, $C_1$-$C_8$ alkoxyl, $C_1$-$C_8$ alkylcarbonyl, halogen, hydroxyl, amino, nitro, and cyano; and
  Y is selected from the group consisting of $C_1$-$C_4$ alkyl with the proviso that if there is a double bond adjacent to the R group, then R is not a phenyl ring substituted by OCH3; and
a carrier, said compound being dissolved or distributed in said carrier.

12. The composition of claim 11, wherein said substituted aromatic or heteroaromatic group is substituted with a hydroxyl or a substituted or unsubstituted amino group.

13. The composition of claim 11, wherein said substituted or unsubstituted aromatic or heteroaromatic group is a substituted or unsubstituted heteroaromatic group which includes an oxygen or a nitrogen as a heteroatom.

14. The composition of claim 12, wherein the substituted or unsubstituted aromatic or heteroaromatic group is further substituted with a substituent selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano.

15. The composition of claim 13, wherein the aromatic or heteroaromatic group is further substituted with a substituent selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano.

16. The composition of claim 11, having the general formula of formula I:

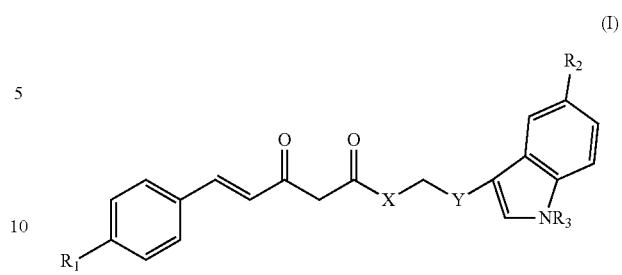

wherein R1 is selected from the group consisting of: H, OH and $NH_2$ and substituted-N wherein the substituent is selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano.

17. The composition of claim 11, having the general formula of formula II:

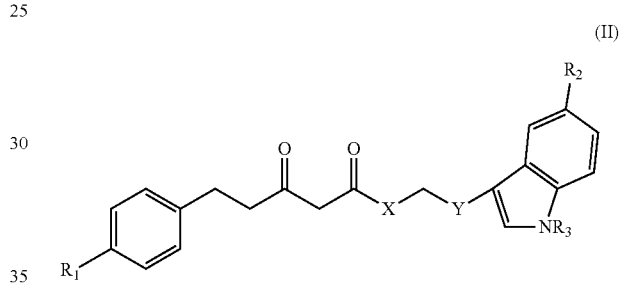

wherein R1 is selected from the group consisting of: H, OH and $NH_2$ and substituted-N wherein the substituent is selected from the group consisting of $C_1$-$C_8$ alkyl, wherein the phenyl is optionally substituted with one or more substituents at positions 2, 3, 5, and 6 selected from the group consisting of $C_1$-$C_8$ alkyl, $C_1$-$C_8$ alkoxyl, $C_1$-$C_8$ alkylcarbonyl, halogen, hydroxyl, amino, nitro, and cyano.

18. The composition of claim 11, wherein said compound is 5-(4-Hydroxy-3-methoxy-phenyl)-3-oxo-pent-4-enoic acid [2-(5-methoxy-1H-indol-3-yl)-ethyl]-amide.

19. The composition of claim 11, wherein said compound is 5-(4-hydroxy-phenyl)-3-oxo-pentanoic acid [2-5-methoxy-1H-indole-3-yl)-ethyl]-amide.

20. The composition of claim 11, wherein said compound is 5-(4-hydroxy-phenyl)-3-oxo-pentanoic acid [2-5-methoxy-1H-indole-3-yl)-ethyl]-amide.

21. The composition of claim 11, wherein said carrier is a solid.

22. The composition of claim 11, wherein said carrier is a liquid.

23. The composition of claim 11, wherein said carrier is an aqueous liquid.

24. A method of treating or slowing the progression of symptoms of a neurodegenerative disorder in a patient in need thereof, comprising the step of administering to said patient a therapeutically effective amount of at least one of a compound having the general formula:

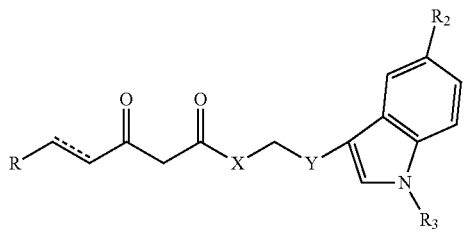

wherein

R is an aromatic or heteroaromatic group;

R2 is selected from the group consisting of H, OH, $NH_2$, $NO_2$ and $C_1$-$C_8$ alkoxyl;

R3 is selected from the group consisting of H and $C_1$-$C_4$ alkyl;

X is S or O or NH or substituted-N, wherein the substituent is selected from the group consisting of $C_1$-$C_8$ alkyl, isopropyl, tert-butyl, and a saturated or unsaturated monocyclic ring with ring size ranging from 3-7 which is optionally substituted with one or more substituents selected from the group consisting of $C_1$-$C_8$ alkyl, $C_1$-$C_8$ alkoxyl, $C_1$-$C_8$ alkylcarbonyl, halogen, hydroxyl, amino, nitro, and cyano; and Y is selected from the group consisting of $C_1$-$C_4$ alkyl with the proviso that if there is a double bond adjacent to the R group, then R is not a phenyl ring substituted by OCH3.

25. The method of claim 24, wherein said neurodegenerative disorder is Alzheimer's disease.

26. The method of claim 24, wherein said compound is compound 5-(4-hydroxy-phenyl)-3-oxo-pentanoic acid [2-(5-methoxy-1H-indol-3-yl)-ethyl]-amide represented by Formula (III):

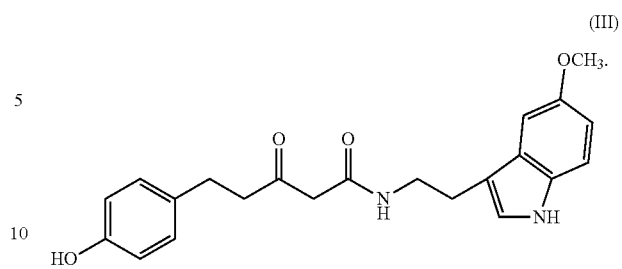

27. The method of claim 24, wherein said compound is 5-(4-hydroxy-phenyl)-3-oxo-pent-4-enoic acid [2-95-methoxy-1H-indole-3-yl)-ethyl]-amide represented by Formula (IV):

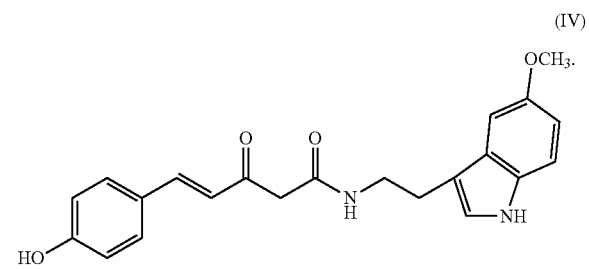 [SMILES: COc1ccc2[nH]cc(CCNC(=O)CC(=O)/C=C/c3ccc(O)cc3)c2c1]

28. The compound of claim 1, wherein the unsaturated monocyclic ring is an unsubstituted or substituted phenyl ring.

29. The composition of claim 11, wherein the unsaturated monocyclic ring is an unsubstituted or substituted phenyl ring.

30. The method of claim 24, wherein the unsaturated monocyclic ring is an unsubstituted or substituted phenyl ring.

* * * * *